(12) United States Patent
Prescott et al.

(10) Patent No.: US 9,706,754 B2
(45) Date of Patent: Jul. 18, 2017

(54) MULTI-CHAMBER, MULTI-FORMULATION FLUID DELIVERY SYSTEM

(71) Applicant: Merial Limited, Duluth, GA (US)

(72) Inventors: Todd Luepke Prescott, Suwanee, GA (US); Rodney Gordon Walker, Hamilton (NZ); Gareth Nigel Lauchlan, Auckland (NZ); David Andrew Trow, Hamilton (NZ)

(73) Assignee: MERIAL, INC., Duluth, GA (US)

( * ) Notice: Subject to any disclaimer, the term of this patent is extended or adjusted under 35 U.S.C. 154(b) by 260 days.

(21) Appl. No.: 14/488,968

(22) Filed: Sep. 17, 2014

(65) Prior Publication Data

US 2015/0128873 A1    May 14, 2015

Related U.S. Application Data

(60) Provisional application No. 61/878,860, filed on Sep. 17, 2013.

(51) Int. Cl.
*A01K 13/00* (2006.01)
*A61D 7/00* (2006.01)
(Continued)

(52) U.S. Cl.
CPC .............. *A01K 13/003* (2013.01); *A61D 7/00* (2013.01); *A61M 5/19* (2013.01); *A61M 5/2066* (2013.01); *A61M 5/3007* (2013.01); *A61M 5/3148* (2013.01); *B05C 17/00576* (2013.01); *B05C 17/01* (2013.01); *A61M 2005/2026* (2013.01);
(Continued)

(58) Field of Classification Search
None
See application file for complete search history.

(56) References Cited

U.S. PATENT DOCUMENTS

| 3,592,385 A | * | 7/1971 | Smith | ................. A01M 7/0092 239/10 |
| 4,669,425 A | * | 6/1987 | Cook | ..................... A23N 17/00 119/670 |

(Continued)

FOREIGN PATENT DOCUMENTS

| AU | 2003236471 | 8/2003 |
| AU | 2004202449 | 6/2004 |

(Continued)

*Primary Examiner* — David Parsley
(74) *Attorney, Agent, or Firm* — Judy Jarecki-Black; Chad Kitchen; Merial, Inc.

(57) ABSTRACT

The application discloses a multi-chamber, multi-formulation fluid delivery system, comprising a multi-chamber applicator in fluid communication with multi-chamber packaging. Applicators according to the instant disclosure have reduced squeeze-strength requirements, and are useful for dispensing fluids, including medicaments, to animals, including livestock animals. The multi-chamber packaging provides separate storage for formulations containing incompatible active ingredients, and is suitable for use with the multi-chamber applicator. The application also discloses methods for using the system to simultaneously deliver multiple active ingredients, at least some of which are not suitable for co-formulation, thus reducing the time, economic burden and animal stress involved with applying multiple, separate formulations to animals.

31 Claims, 26 Drawing Sheets

(51) Int. Cl.
*A61M 5/19* (2006.01)
*B05C 17/005* (2006.01)
*B05C 17/01* (2006.01)
*A61M 5/20* (2006.01)
*A61M 5/30* (2006.01)
*A61M 5/31* (2006.01)

(52) U.S. Cl.
CPC ............. *A61M 2005/3103* (2013.01); *A61M 2005/3115* (2013.01); *A61M 2005/3128* (2013.01)

(56) References Cited

U.S. PATENT DOCUMENTS

| | | | | |
|---|---|---|---|---|
| 4,790,454 | A * | 12/1988 | Clark | A01C 23/042 222/136 |
| 5,152,461 | A * | 10/1992 | Proctor | B05B 11/0018 222/136 |
| 5,199,604 | A * | 4/1993 | Palmer | A61C 1/0084 222/136 |
| 5,402,916 | A * | 4/1995 | Nottingham | B05B 11/3004 222/134 |
| 5,769,275 | A * | 6/1998 | Boehmer | B05B 11/0016 222/136 |
| 5,887,761 | A * | 3/1999 | Foster | B05B 11/007 222/383.1 |
| 5,906,318 | A * | 5/1999 | Gurko, III | B05B 7/2472 222/136 |
| 6,036,057 | A * | 3/2000 | Poutiatine | B05B 11/0056 222/137 |
| 6,082,588 | A * | 7/2000 | Markey | B05B 11/3084 222/135 |
| 6,283,385 | B1 * | 9/2001 | Beaver | B05B 7/2472 239/10 |
| 8,474,659 | B2 * | 7/2013 | Dennis | B05B 15/005 222/137 |
| 8,584,899 | B2 * | 11/2013 | Dessaint | B29B 11/14 215/40 |
| 9,180,476 | B2 * | 11/2015 | Werner | B05B 11/3083 |
| 2010/0019062 | A1 * | 1/2010 | Clarke | A01M 21/043 239/373 |
| 2010/0025494 | A1 * | 2/2010 | McDonald | A01M 7/0046 239/310 |

FOREIGN PATENT DOCUMENTS

| | | |
|---|---|---|
| AU | 2012202192 | 4/2012 |
| AU | 2013100370 | 3/2013 |
| AU | 2013201891 | 3/2013 |
| CA | 2267812 A1 | 10/2000 |
| GB | 2 172 937 | 10/1986 |

\* cited by examiner

MULTI-CHAMBER, MULTI-FORMULATION FLUID DELIVERY SYSTEM

INCORPORATION BY REFERENCE

This application claims priority to US provisional application No. 61/878,860, filed on Sep. 17, 2013, and herein incorporated by reference in its entirety. All other references cited herein are likewise incorporated by reference herein in their entirety.

FIELD OF THE INVENTION

The present invention relates to multi-chamber fluid delivery systems comprising applicators, connecting means, and multi-chamber packaging. In particular, the invention relates to systems useful in delivering liquid formulations, including medicaments and parasiticides, to animals in need thereof.

BACKGROUND OF THE INVENTION

Animal remedies for sheep, cattle and other livestock/production animals are applied by a number of methods including topical or "pour-on" application, oral "drench" application, injection and nasal infusion. Each of these administration routes is typically dispensed from a "pistol grip" style dispensing means. Such an applicator is described in the applicant's New Zealand patent No. 521084, the contents of which are herein incorporated by reference.

Conventional fluid applicators have incorporated two, one-way valves (inlet and outlet). Such valves are typically biased with springs, so that they open only when there is a predefined difference in the fluid pressure between the upstream side of the valve and the downstream side. Fluid cannot flow backwards through either valve, as flow in this direction will tend to push the valves more tightly closed. When the applicator is at rest, both valves are closed. When the applicator is in use, it is intended that only one valve opens at a time. During the discharge stroke, the outlet valve is pushed open by the raised fluid pressure within the barrel. During the refill stroke, the inlet valve is pushed open by fluid entering the barrel (where there is now a partial vacuum).

A problem with conventional applicators is that they require a relatively large force to squeeze the handles together during the application stroke of the piston. This may be fatiguing for the operator, particularly when the applicator is used to treat a large group of animals. In response to this problem, Applicants developed the BREAZE™ Technology, which is fully disclosed in patent AU 2013100370, the contents of which are herein incorporated by reference it their entirety. FIGS. 1-2 depict some of the key features of the BREAZE™ applicator, which requires a significantly smaller amount of force to squeeze as compared to predecessor dosing gun devices.

Although the BREAZE™ technology significantly improved upon "harder to squeeze" prior art devices, it would be useful to build on this technology to develop an applicator which allows for the delivery of two or more fluids. Such a device would allow for more efficient delivery of fluids that must be stored separately (e.g. active ingredient substances which are not readily co-formulated). Moreover, it would be desirable to develop devices capable of delivering even larger volumes of fluid, while maintaining the low squeeze strength requirement of the original, single chamber, single formulations BREAZE™ applicators. Finally, to produce acceptable ergonomics for such a device, it would be highly desirable to reverse the applicator's configuration, such that the dosing chambers/barrels are situated above the users wrist instead of in front of the applicator.

SUMMARY OF THE INVENTION

It is an object of the invention to provide a multi-chamber, multi-formulation fluid delivery system (hereinafter, "the System"), comprising a multi-chamber applicator in fluid communication with a multi-chamber package. The applicator has reduced squeeze-strength requirements, and is useful for dispensing fluids, including medicaments, to animals, including livestock animals. The multi-chamber packaging provides separate storage for formulations containing incompatible active ingredients, and is suitable for use with the multi-chamber applicator.

It is another object of the invention to provide methods for using the System to simultaneously deliver multiple active ingredients, at least some of which are not suitable for co-formulation. For example, it is well-known that Macrocyclic lactone parasiticides are particularly sensitive to acid hydrolysis, so combining them with water-soluble anthelmintics (e.g. levamisole) has been extremely difficult. In fact, co-formulation of some active ingredients has proved so challenging that many parasiticide/pesticide manufacturers have opted to supply incompatible compounds as separate formulations/product offerings, even though simultaneous delivery is highly desired by customers. The inventive simultaneous delivery methods offer a solution to this problem by providing both a financial advantage (i.e. reducing the time it takes to apply medicaments by more than half), and by providing a way to achieve an improved clinical effect (e.g. speed or duration of parasiticidal/pesticidal activity), where simultaneous active ingredient delivery is the only or best way to achieve such an effect. Moreover, simultaneous formulation delivery is less stressful to the animals than separate/sequential formulation delivery.

Other objects of the present invention may become apparent from the following description, which is given by way of example only.

DESCRIPTION OF THE INVENTION

Figure 1:
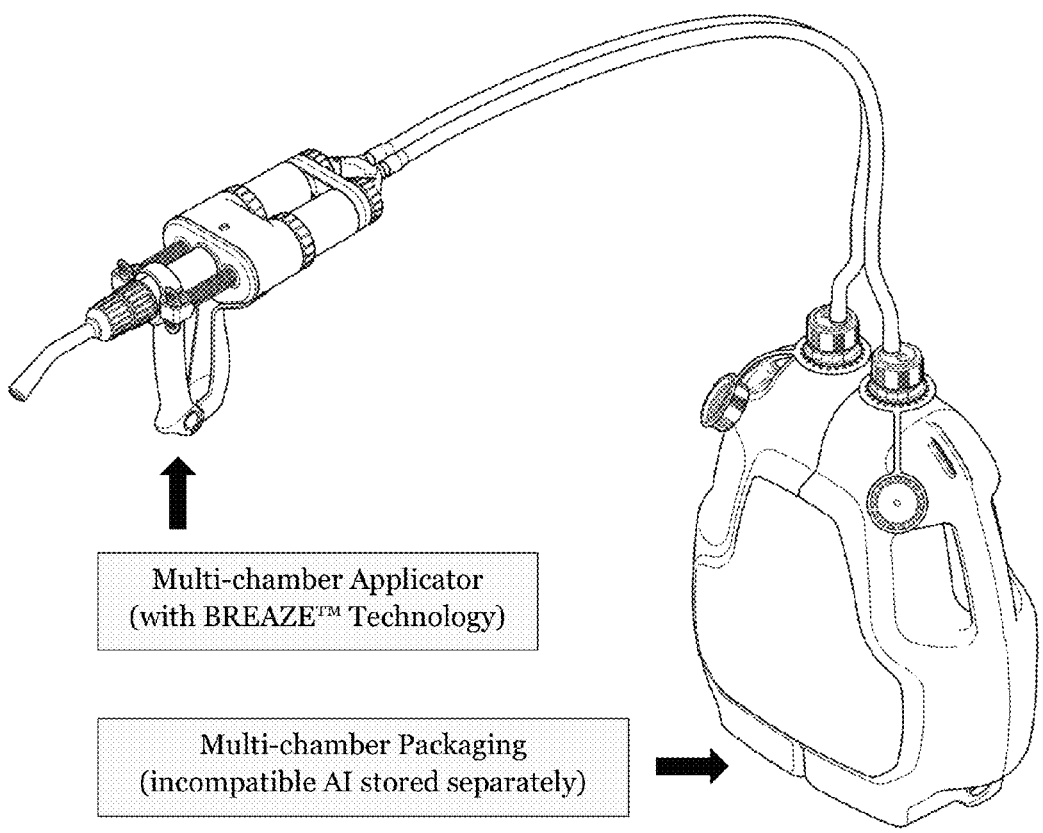
FIG. 1 depicts a Multi-chamber, Multi-formulation Delivery System according to the disclosure.

Throughout the description and the claims, all reference to pressures are to gauge pressures, i.e. pressure relative to the ambient pressure. Therefore, a reference to zero pressure means ambient pressure. Reference to negative pressure means suction. Reference to a partial vacuum is any pressure below ambient pressure but greater than a total vacuum.

Reference to the "upstream" direction is towards the direction in the fluid flow path from which fluid enters the applicator. Reference to the "downstream" direction is to the direction in which the fluid normally flows.

The reference to any prior art in the specification is not, and should not be taken as, an acknowledgement or any form of suggestion that the prior art forms part of the common general knowledge in any country.

According to one aspect of the present invention there is provided a Multi-chamber System comprising a multi-chamber applicator and multi-chamber packaging.

In an embodiment, the applicator comprises:
  at least two fluid supply inlets;
  at least one outlet;
  at least two barrels each having barrel outlets and barrel inlets which are in fluid communication, or selective fluid communication, with the fluid supply inlets;
  at least two one way outlet valves, one for each barrel, in fluid communication with the barrel outlets and with the outlets;
  at least two pistons, one for each barrel, moveable relative to the barrels and in sealing engagement with the barrels;
  a piston actuation means for moving the pistons relative to the barrels;
  at least two pressure limiting means for limiting a maximum pressure of fluid entering the barrels from the fluid supply inlets;
  a means for combining the fluids from the at least two barrels into a single outlet.

In a particular embodiment, the applicator further comprises a means for selecting the volume of fluid that is drawn into each barrel from a reservoir, contained within a multi-chamber active ingredient formulation package.

In an embodiment, the pressure limiting means is configured such that the fluid entering the barrels has a pressure which is at or below an ambient atmospheric pressure.

In another embodiment, the pressure limiting means is configured such that the fluid entering the barrels has a pressure which is at or below a pressure required to open the outlet valves.

In an embodiment, the pressure limiting means are provided at or adjacent the barrel inlets.

In an embodiment, the pressure limiting means are fixed at the entrance or base of the barrels.

In a particular embodiment, the pressure limiting means comprise diaphragms.

In an embodiment, each diaphragm is annular in shape. A first side of each diaphragm may be in fluid communication, or selective fluid communication, with fluid in each barrel. In such an embodiment, each opposite second side of each diaphragm is exposed to ambient atmospheric pressure.

In an embodiment, displacement of the diaphragm changes an internal volume of a conduit supplying fluid to the barrel inlets.

In a particular embodiment, the applicator is provided with a one way valve means for preventing fluid flow from each barrel though its respective barrel inlet.

In an embodiment, the pressure limiting means is adapted to prevent fluid flow from the barrel inlet to the fluid supply inlet.

Each barrel's corresponding pressure limiting means may comprise a first valve head and a first valve seat, wherein the first valve head can be moved from a closed position to an open position by movement of the diaphragm. In a particular embodiment, each pressure limiting means comprises a second valve head and second valve seat, wherein the second valve head is connected to the first valve head and moves with the first valve head. In such an embodiment, a pressure difference across said first valve head is substantially equal to a pressure difference across said second valve head.

In a particular embodiment, the pressure difference across said first valve head creates a resultant force in a first direction and the pressure difference across said second valve head creates a resultant force in a second direction which is opposite to the first direction.

In an embodiment, the resultant forces are substantially equal, for each barrel.

In an embodiment, the resultant force on the second valve head is greater than the resultant force on the first valve head, for each barrel.

According to another aspect of the present invention there is provided a Multi-chamber, Multi-formulation Delivery System (hereinafter "the System") comprising an applicator and at least two fluid supply conduits with required connectivity, and a Multi-chamber, Multi-formulation Packaging, comprising multiple independent fluid reservoirs filled with formulations. In a particular embodiment, the formulations contain one or more active ingredients, which cannot be combined into a single, shelf stable formulation.

According to a further aspect of the present invention there is provided a Multi-chamber, Multi-formulation Delivery System substantially as herein described with reference to any one of FIGS. 2 to 8. The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth. Further aspects of the invention, which should be considered in all its novel aspects, will become apparent from the following description given by way of example of possible embodiments of the invention.

The invention will now be described in the following non-limiting Examples.

EXAMPLES

Multi-Chamber, Multi-Formulation Fluid Delivery System

In a particular embodiment, the invention provides a Multi-chamber, Multi-formulation Delivery System (hereinafter "the System"), substantially as depicted in FIG. 1.

In an embodiment, the System comprises:
(a) a multi-chamber applicator for delivering multi-formulations to an animal;
(b) suitable conduit and connectivity for connecting the applicator to fluid packaging; and
(c) multi-chamber package for separately containing and storing formulations.

Figure 5:
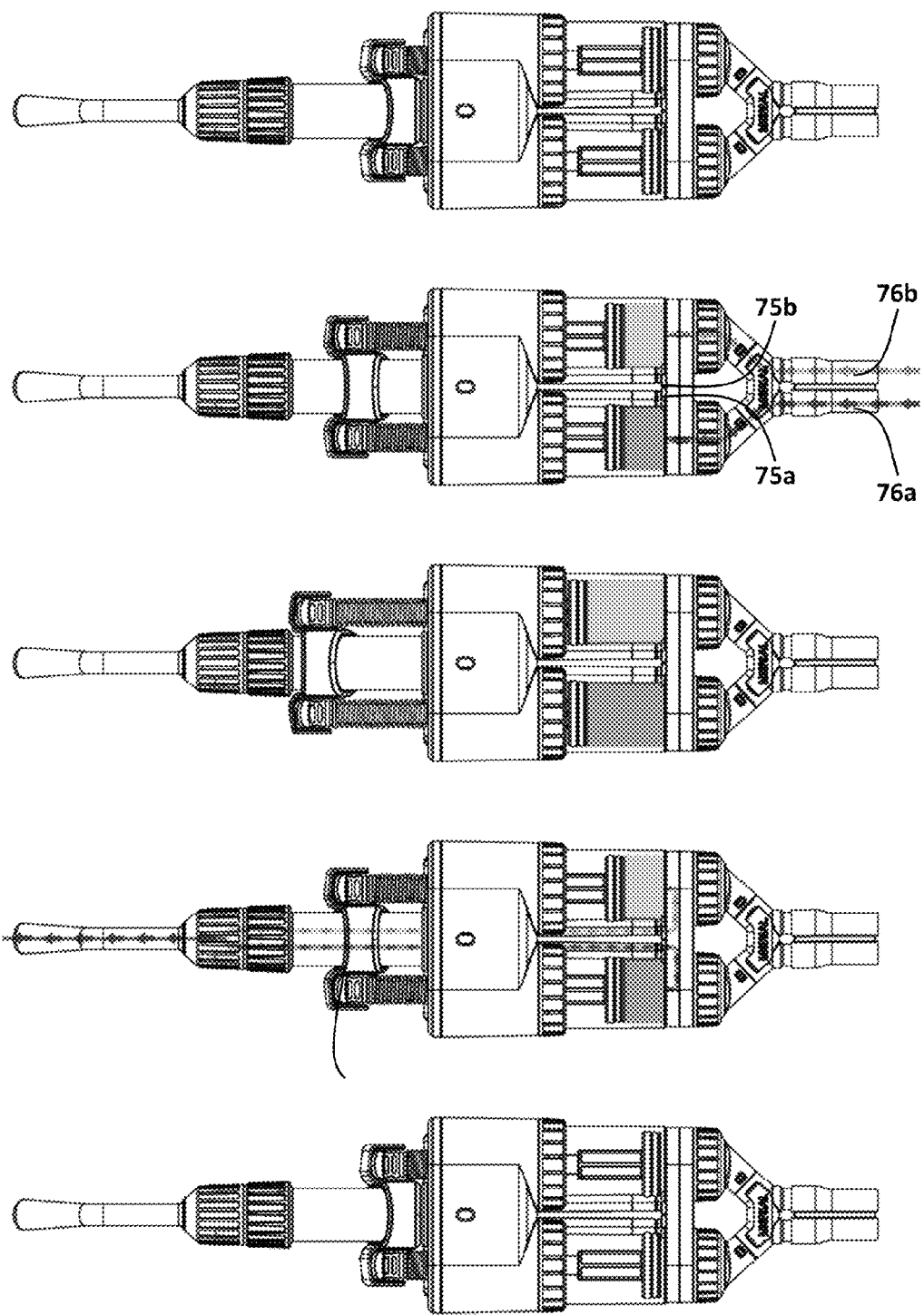
FIG. 5 is a schematic diagram depicting the operation and fluid flow path of a multi-chamber applicator according to the instant disclosure.

In a particular embodiment, the applicator is substantially as depicted in FIGS. 3 and 5, and as described below. The applicator may be connected to the multi-chamber packaging by conduits, which are color-coded (or otherwise marked) to reduce the chance of combining incompatible formulations in the connecting conduits or the applicator chambers.

Multi-Chamber Applicator

Referring to FIGS. 2A, 2B, 3A-D and 5, an applicator according to one embodiment of the present invention is generally referenced by arrow 200. Hereinafter, whenever the disclosure refers to numerical identifiers for the various Figures, "a" shall refer to the components present in the chamber assembly depicted in the lower portion of FIG. 3A, while "b" shall refer to the corresponding "twin" component depicted in the upper portion of FIG. 3A. Where not explicitly stated, it is intended that reference to any component that is present in both the "a" and "b" barrel assembly, "#" shall be understood to mean "#a/b." For example, reference to "conduit 13" shall be understood to be equivalent to reference to "conduit 13a/b." Moreover, in reading this disclosure, an ordinarily skilled person will instantly be able to produce a device with two (a/b), three (a/b/c), four (a/b/c/d), five (a/b/c/d/e), six (a/b/c/d/e/f), or any higher number of barrel assemblies, without the exertion of inventive activity. The inventors also envision applicators that do not mix the two or more formulations in advance of the fluid streams making contact with a target patient/animal. For example, the multi-chamber applicator may have more than one outlet, including two, three, four, or any higher number of outlets. Such a configuration would be highly advantageous where the two or more formulations are so incompatible that mixture of same prior to release from the applicator could cause unacceptable clogging, corrosion, or other types of damage dispensing conduits.

Figure 3A:
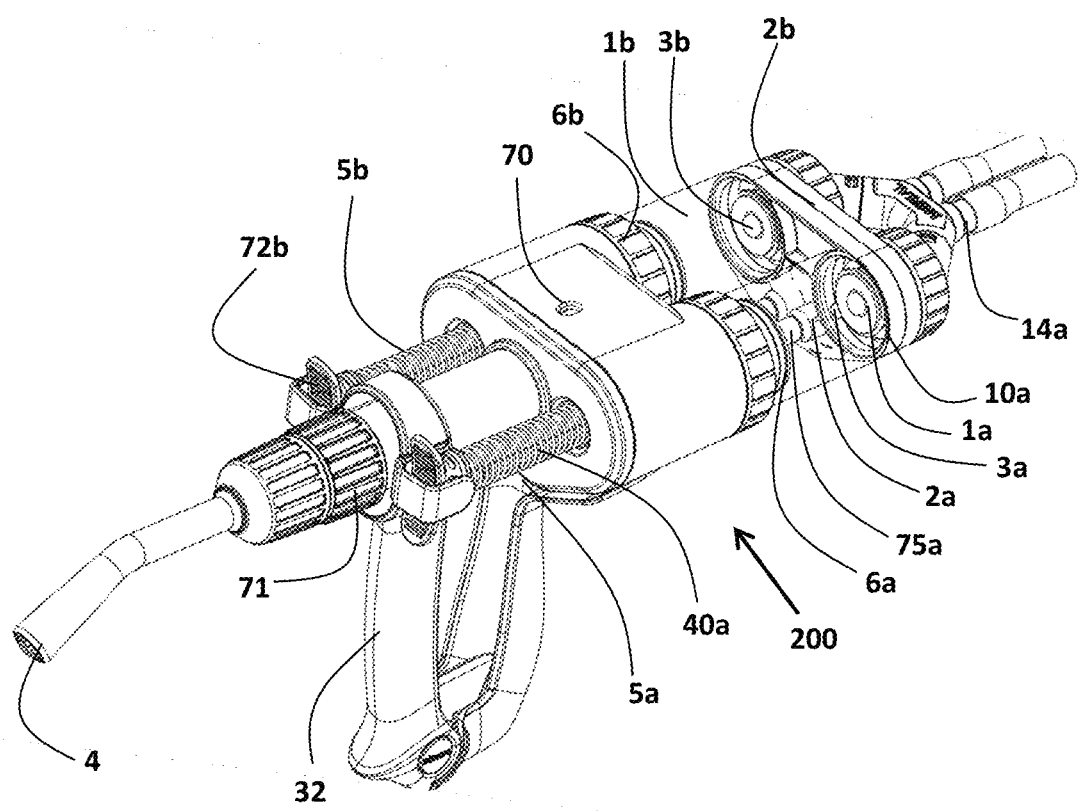
FIG. 3A depicts an applicator (200) according to the disclosure, which comprises the valve means and pressure limiting means depicted in FIGS. 2A and 2B.

In the embodiment depicted in FIG. 3A, the applicator 200 has a first barrel (1a) with an outlet (2a). A one way outlet valve (3a) is provided at or adjacent the barrel outlet (2a). The barrel outlet (2a) is in selective fluid communication with an applicator outlet (4) from which fluid is discharged in use. In other embodiments (not shown) the one way valve (3a) may be integrated with the valve means (12a). Correspondingly, the applicator has a second barrel (1b) with an outlet (2b). A one way outlet valve (3b) is provided at or adjacent the barrel outlet (2b). The barrel outlet (2b) is in selective fluid communication with an applicator outlet (4) from which fluid is discharged in use. In other embodiments, the one way valves (3a/b) are located at the connection between the nozzle and the applicator, at the end of the conduits (75a/b) (i.e. at point "X" in FIG. 5). The applicator could also have additional barrels, wherein the "nth" barrel (1x) with an outlet (2x). A one way outlet valve (3x) is provided at or adjacent the barrel outlet (2x). The barrel outlet (2x) is in selective fluid communication with an applicator outlet (4) from which fluid is discharged in use, wherein "n" is an integer greater than 3 and "x" is a small letter c-z.'

In a particular embodiment, the fluids combine once they have passed the two one-way valves, (3a/b). In another embodiment, the fluid streams may combine just prior to exiting the applicator (200) at the outlet (4).

A piston or plunger (5) is located within the corresponding barrel (1) and has corresponding sealing means (6), for example an O-ring seal, to sealingly engage a corresponding inner surface (7) of the barrel (1).

In an embodiment, the piston (5) is connected to or has an integrated pushrod (8) and a substantially cylindrical head (9) that travel along the cylindrical barrel. When the handle (32) is squeezed, the pushrod moves the piston along the cylindrical barrel (1) such that the distance between the head of the piston (5) and the valve means (12) is reduced. When the handle (32) is released, this distance increases. Initial squeezing of the handle (32) prepares the applicator (200) for receiving fluid into each of its chambers/barrels (1). Releasing the handle (32) causes fluid to be drawn through the valve means (12) into the barrel (1). Alternatively, each barrel may be individually primed by pressing and releasing each of the barrel plungers. Subsequent squeezing of the handle (32) dispenses the fluid by forcing it to pass through the one-way valve (3), through the barrel outlet (2), and into the dispensing conduit (75). The two dispensing conduits (75a/b) may meet (e.g. at a "Y" junction) to combine the fluids just prior to exiting the applicator (200) via the outlet (4). Alternatively, the conduits (75a/b) may remain separate, terminating into two separate dispensing tips, instead of combining at point "X" as shown in FIG. 5.

Figure 2A:
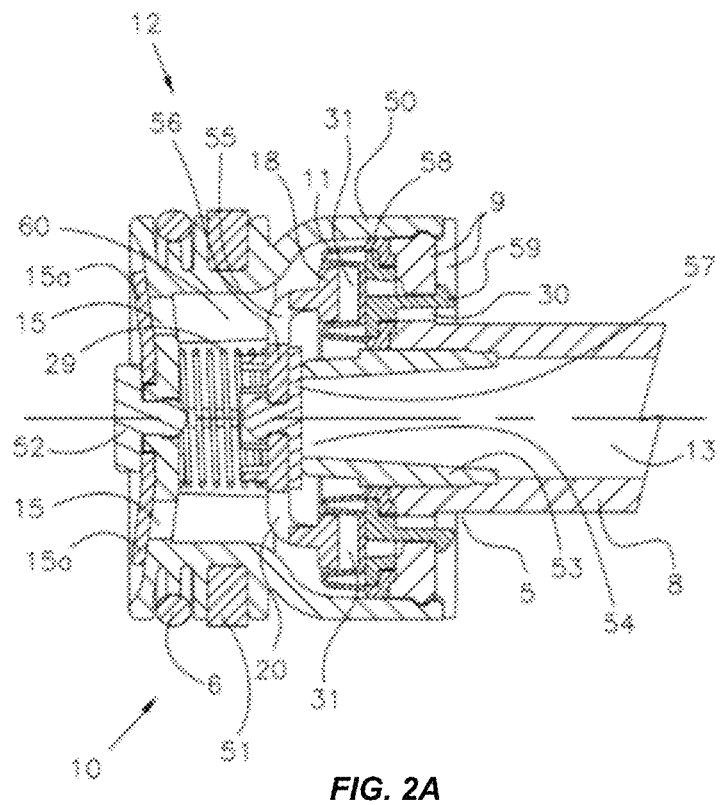
FIG. 2A is a cross-section side view of a pressure limiting means and valve means of a Multi-chamber Applicator according to the disclosure (valve closed)

Fluid travels to each applicator barrel (1) via a filling conduit (76), which is removably attached to an inlet (14). From the inlet (14) the fluid enters the barrel (1) through a pressure limiting means (10) and the valve means (12), as depicted in FIGS. 2A (valve closed), 2B (valve open), 3 and 4. In an embodiment, the pressure limiting means (10) comprises a flexible diaphragm (11) connected to the valve means (12). In the embodiment shown, a one way valve means (15a) is provided to prevent flow from the barrel (1) towards the inlet (14).

In this embodiment the outlet valve (3) is of a type commonly known as an umbrella valve, selected because of its ability to open at relatively low pressure and therefore reduce the squeeze force required to be applied to handle (32). A valve incorporating a spring could be used instead, as could any other reasonable valve known to those of skill in the art. In this embodiment the one way valve (15a) is a valve disc which is held in place by a pin (52). Rigid tubing (77) connecting the inlet (14) to the barrel (1) comprises a jet component (53), which defines an orifice 54 for fluid to flow into the pressure limiting means (10) and the valve means (12).

An annular diaphragm (11) is clamped to the tubing (77) by a clamp ring (58), held in place by integral clips (59). The clips 59 pass through apertures (30) in the base of the tubing, where the tubing meet the base of the barrel (1). These apertures (30) also provide venting to one side of the diaphragm (11).

A force transfer component (55) has an outer ring or hub (18), which is (in FIG. 2A/2B) separated from the diaphragm (11) by clearance space (31). The force transfer component (55) has multiple spokes (20) which connect the outer hub (18) to an inner portion (56) which carries a sealing washer (57).

A spring (29) biases the force transfer component (55) and the sealing washer (57) against the jet (53), blocking the orifice (54). In this way the sealing washer (57) functions as a valve head (22), and the end of the jet component (53) functions as a valve seat (24). A plurality of radially inwardly extending fins (60) define a guide for the spring (29) and the force transfer component (55). The fins (60) may also limit the maximum travel of the force transfer component (55), when the outer rim (18) contacts the fins (60). In this way the fins (60) may limit the opening of the sealing washer (57) from the jet component (53), thereby limiting the flow rate of fluid (61) travelling through the inlet conduits into the barrel. By limiting this flow rate, the magnitude of the pressure pulse created at the end of the refilling stroke is limited.

The use of the diaphragm (11) to provide an opening force on the sealing washer (57) means that the spring (29) can be configured to provide a relatively high closing force, thereby reducing the likelihood that the pressure pulse created when the piston reaches the end of the refilling stroke will pass into and through the barrel. The ability of the diaphragm itself to deflect (effectively increasing the volume of the inlet conduit), thereby absorbing any small amount of fluid which the pressure pulse does force past the pressure limiting means valve head, also reduces the likelihood that fluid will leak from the outlet valve, even if the fluid pressure required to open the outlet valve is low compared to the applicators of the prior art.

The force of spring (29) is sufficient to hold valve (12) closed against the pressure of the fluid in the rigid tubing (77), even if the fluid reservoir (see FIG. 1 and below description of the Multi-chamber packaging) which supplies fluid to the fluid inlet (14) is raised a limited distance above the applicator (200).

When the user operates the actuating means (32) to drive the piston (5), the piston 5 is pushed backwards, towards the user's body, and displaces fluid which flows through the one way outlet valve (3). The multiple streams of fluid then flow through the dispensing conduits (75), combine at the dispensing conduit junction (80), and exit out through the outlet (4). The force required to open the outlet valve (3) causes the pressure inside the barrel (1) to rise above atmospheric pressure. The one way valve (15a) prevents this pressure from pushing the diaphragm (11) rearwards. The diaphragm (11) does not move from the position shown in FIG. 2A during this phase of operation. Valve (12) is still held closed by spring (29). In particular embodiments, the outlet valve (3) is configured to open under a lower pressure than the outlet valves of conventional applicators. This reduces the pressure of the fluid within the barrel during the application stroke, and hence reduces the required hand squeeze force on the handle (32).

When the user releases the handle (32), a biasing means, for example a piston spring (40) provided circumscribing the piston (5), pulls the piston (5) forwards. This induces a partial vacuum inside the barrel (1), which is communicated to the diaphragm (11) through the inlet (15) and one way valve (15a). Air pressure acting on the rearward-facing side of the diaphragm (11) pushes the diaphragm forwards, closing clearance space (31). The diaphragm (11) then pushes forwards against the force transfer component (55). When the pressure of the fluid in the barrel (1) is low enough, the force generated by the diaphragm (11) overpowers the spring (29) and moves the valve head (22) away from the valve seat (24), as shown in FIG. 2B, thereby allowing fluid to flow through the valve (12).

The distance that the valve (12) opens depends (amongst other things) on how low the pressure in the barrel (1) is. The valve (12) may open fully, or only part-way. In some embodiments, the stiffness of the diaphragm (11) may cause it to act like a spring, adding to the biasing force created by spring (29).

Figure 2B:
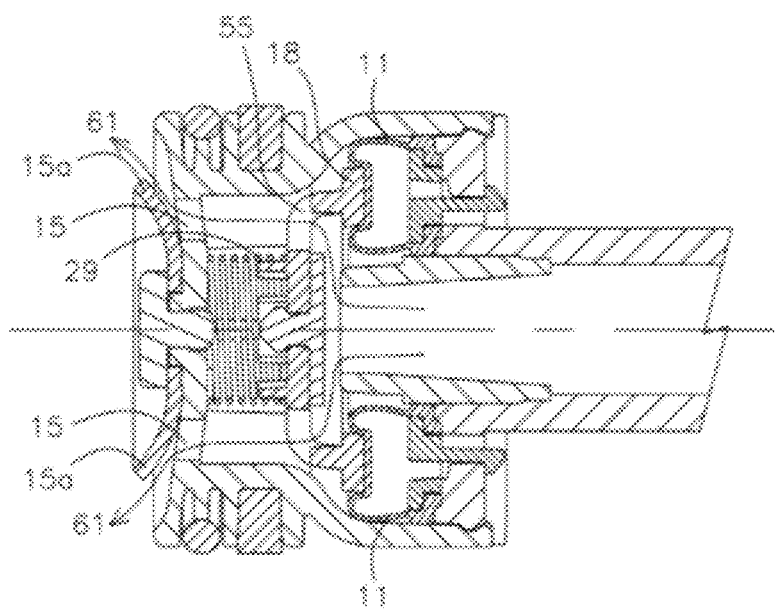
FIG. 2B is the cross-section with the pressure limiting valve means open.

FIG. 2B shows the assembly with the diaphragm (11) deflected and the valve (12) fully open. This occurs when the piston (5) is being retracted and the barrel (1) is filling with fluid through the valve (12) and inlet (15). At the end of the barrel refilling stroke the piston (5) contacts a fixed stop. The stop is typically part of a variable dosage control means (71). Suitable dosage control means are known to the art, and include that described in applicant's New Zealand patent number 521084, the contents of which are included herein by reference.

The momentum of the fluid flowing into the force limiting means (10) and valve (12) via rigid tubing (77) and in the upstream supply tube (76, depicted in FIGS. 1 and 5) may tend to keep the fluid moving past the valve (12) and into the barrel (1), even though the spring (29) is acting on the valve head (22) to try to close the valve (12). If this occurs, the pressure in the barrel (1) rises and the diaphragm (11) moves rearward, pulled back by the spring (29) acting on the diaphragm via the force transfer component (55).

The valve (12) returns to its substantially closed position before the rising pressure in the barrel (1) reaches atmospheric pressure. Closure of the valve (12a) may result in a pressure pulse (from a "water hammer" effect, which is known to those of skill in the art) in the tubing (77), and the preceding supply tubing (76). However, the force of the spring (29) is ideally sufficient to keep the valve (12) substantially closed despite the momentary increase in pressure caused by the pressure pulse.

Since the pressure pulse cannot pass the closed valve (12), the problem of fluid discharging from the nozzle during this time is avoided. Since the valve (12) is opened by the diaphragm (11) when necessary, the spring (29) may be selected to provide a larger biasing force than that used by the applicators of the prior art. Assuming that there are no leaks, the pressure in the barrel (1) remains slightly below atmospheric pressure. Because no more fluid can pass the closed valve (12), the diaphragm (11) may remain deflected slightly forwards, touching the force transfer component (55) (i.e. the clearance space (31) is closed).

Those skilled in the art will appreciate that although the pressure in the barrel (1) of the embodiment described above is below atmospheric at the end of the inlet stroke, other embodiments may be configured such that the pressure is at or above atmospheric pressure at that stage. In particular, the water hammer pressure pulse may be large enough to force a small volume of fluid past valve (12), preventing the valve from closing fully, or even reopening it slightly, despite the biasing force of the spring (29). The passage of this small volume of fluid will displace the diaphragm rearward, reopening a gap between the force transfer component (55) and the diaphragm (11). There may be a corresponding rise in the pressure of the fluid in the barrel. While this pressure rise may be mitigated by the increase in available volume caused by the deflection of the diaphragm, in some circumstances the pressure may rise to above atmospheric pressure. However, as long as the pressure within the barrel is not high enough to force the outlet valve (3) open, there will be no unwanted discharge of fluid. Therefore, the ideal applicator should have substantially zero, or zero unwanted discharge of fluid.

In a particular embodiment of the invention, the fluid flows in accordance with the drawings in FIG. 5. The general flow of fluid during typical applicator operation is as follows:

1. Set Dose, Ready the Applicator to Prime—the dose is selected using the dosage selector (71), and the handle is then pulled back to bring both plungers to full extension (regardless of dose setting);

2. Fill Dual Chambers—the handle is released and both plungers (5) retract, creating a vacuum in the dose chambers/barrels (1). Fluid enters both dose chambers through the BREAZE™ twin-valving. Alternatively, the plungers may be pressed back individually, using thumb/finger tabs (72), to fill the chambers/barrels (1);

3. Ready to Use—the plungers (5) are fully retracted and both dose chambers (1) are filled to the selected dose;

4. Pour-on Application—the handle (32) is pulled back and fluid is expelled from both dose chambers first through the outlet valves (3), then into the dispensing conduit (75), and finally out the outlet (4). The fluid streams are combined at junction (80) just prior to exiting through outlet (4);

5. Oral Dose Applied—the handle is pulled back and both plungers are at full extension (regardless of dose setting). The combined product from both dose chambers has been dispensed through alternate oral-delivery nozzle (not shown here, but easily added/adapted by those skilled in the art).

The process is repeated as needed by cycling through either Stages 2 to 4 (for topical application) or Stages 2, 3, and 5 (for oral delivery).

Multi-Chamber Packaging

Figure 6A:
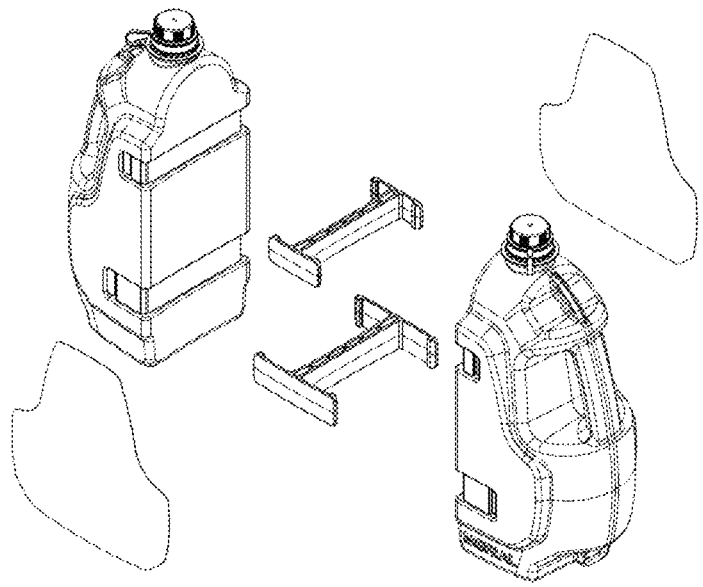
FIG. 6A depicts an embodiment of the multi-chamber packaging, where two separate reservoir "halves" are designed to be brought together using vessel/reservoir interlocks.

In a particular embodiment, the Multi-chamber Packaging is as depicted in FIGS. 1, 6A/6B and 7.

Figure 6B:
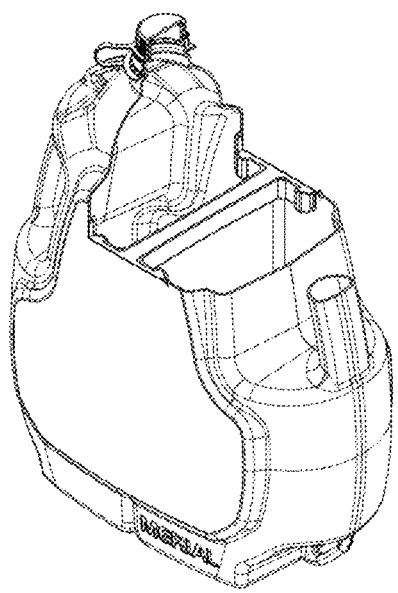
FIG. 6B depicts the two halves connected by the interlocks.
Figure 7:
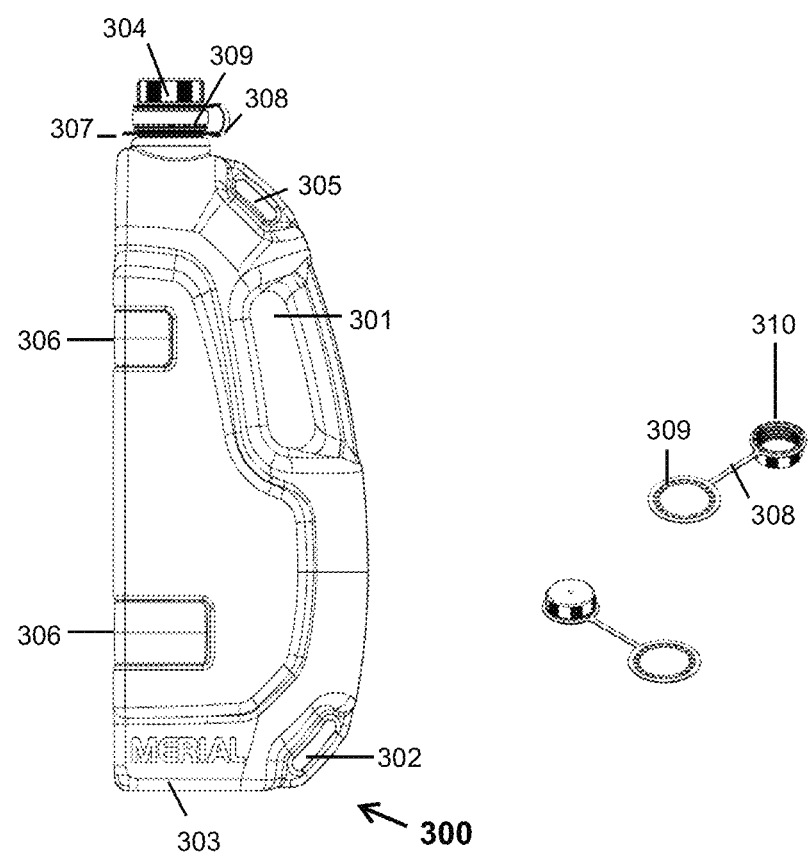
FIG. 7 depicts several features of one chamber (300) of a multi-chamber package according to the invention.

In an embodiment of the multi-chamber packaging shown in FIG. 6B, two separate reservoir "halves" have been designed to be brought together using vessel/reservoir interlocks (306). The embodiment shown in FIG. 7 is one half of a dual-chamber package. The chamber may have a slot (301) that serves as a handle or an attachment for backpack-securing straps. Slot (302) may also serve as an attachment for straps. The chambers may be equipped with travel/transit caps (304), which may be connected to dispenser caps (305).

In an embodiment, a chamber may comprise a tether (308), which secures the transit cap (305) to the packaging neck (307). Ideally, the transit cap (305) rotates freely within the tether ring (309), allowing the two transit caps to be removed or secured to the packaging without twisting the tethers and/or the conduits (76).

In a particular embodiment, each chamber includes a tamper evident ring, which breaks free from the transit cap (305) when transit cap is removed from the packaging.

The packaging may comprise 5 L vessels, hollow-section carry handles, four-point lugs (2 top+2 bottom) for securing the multi-chamber packaging to a user's back with a simple strapping system or a co-packaging harness according to the instant disclosure.

In an embodiment, manufacturing data is provided on each vessel base, including a mold ID, a recycling symbol, and a date stamp. The transit cap may be, for example, 38 mm (one per vessel), and include: a tamper evident induction foil seal and a tether.

In an embodiment, two injection molded 'H' clips secure the two or more vessels/chambers together. Clips may be hidden by a product label, which provides a tamper evident seal.

In an embodiment, each chamber includes an induction foil seal (310), which provides both hermetic seal and secondary tamper evidence when induction sealed to the packaging neck.

Figure 8:
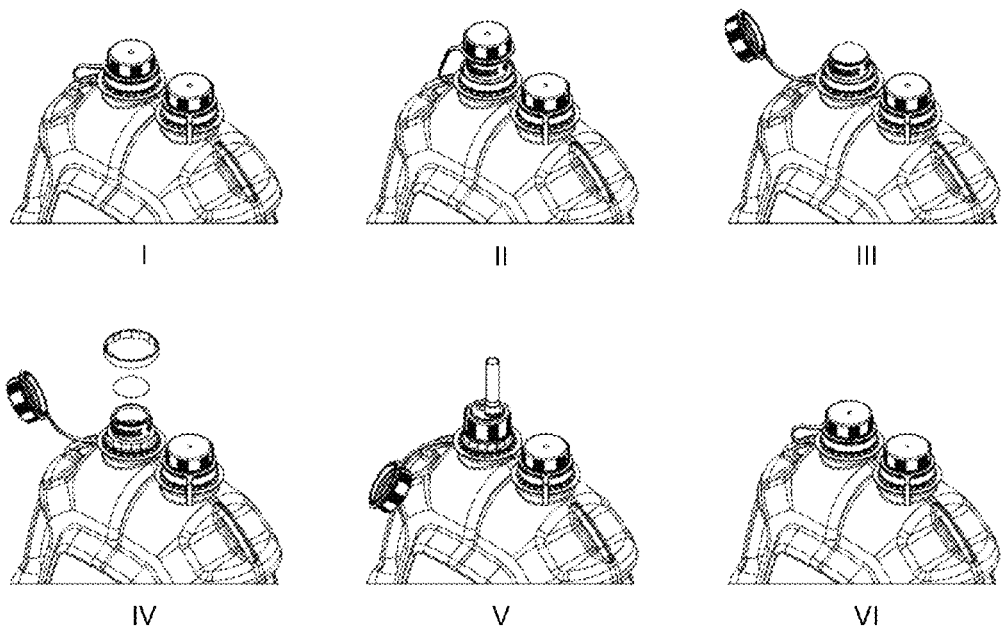
FIG. 8 depicts the configuration of the multi-chamber packaging during shipping/transport (I); use (II-V); and storage (VI)

In an embodiment, the packaging may be used according to scheme presented in FIG. 8:
1. "Shipping Mode"—Tamper evident transit caps fitted to each chamber of the multi-packaging and induction sealed during;
2. Removing transit cap ruptures the tamper evident seal A
3. Foil seal B can now be removed.
4. Discard tamper evident ring A and remove foil seal B. Packaging now opened.
5. Attach the No-Twist Vented Draw-Off Cap C and delivery tube D to packaging. Transit cap remains tethered to packaging neck.
6. Re-attach transit cap to packaging. If the tamper evident ring has been ruptured/removed, the transit cap has been previously removed.

In an embodiment, the cap body provides connection for the delivery tube and a fluid-tight seal to the packaging. Being separated from the Cap Locking Ring, the Cap Body is not subjected to a twisting action when the locking ring is used to secure or remove the No-Twist Draw-Off Cap to/from the packaging. The cap locking ring may fit over the cap body and engage with the packaging neck thread, securing the no-twist draw-off cap to the packaging.

Figure 9:
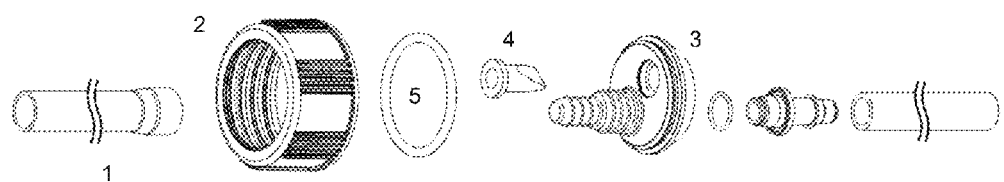
FIG. 9 depicts a no-twist, vented draw-off cap for use with the multi-chamber packaging.

In an embodiment, the packaging includes a draw-off cap (no-twist and vented) substantially as depicted in FIG. 9. Component parts include:
1. A delivery tube, which provides a flexible interconnection between the No-Twist Draw-Off Cap and the Applicator barrel;
2. A Cap Locking Ring, which fits over the Cap Body and when engaged with the packaging neck thread, secures the No-Twist Draw-Off Cap to the packaging ready for use. The draw-off tube connection is not subject to a twisting action, allowing the delivery tube to remain attached to the No-Twist Draw-Off Cap when it is secured to or removed from the packaging.
3. A Cap Body, which provides the delivery tube connection to the No-Twist Draw-Off Cap. The body may comprise a dual 6.4/9.5 mm delivery tube connection, and a cone seal, which provides fluid seal between the No-Twist Draw-Off Cap and the packaging;
4. An Air bleed valve, which allows the co-packaging pressure (vacuum) to equalize with the atmosphere when the product is being removed during application; and
5. Optionally, an O-ring, which can be fitted inside the Cap Body cone seal for additional fluid sealing provision.

Figure 10:
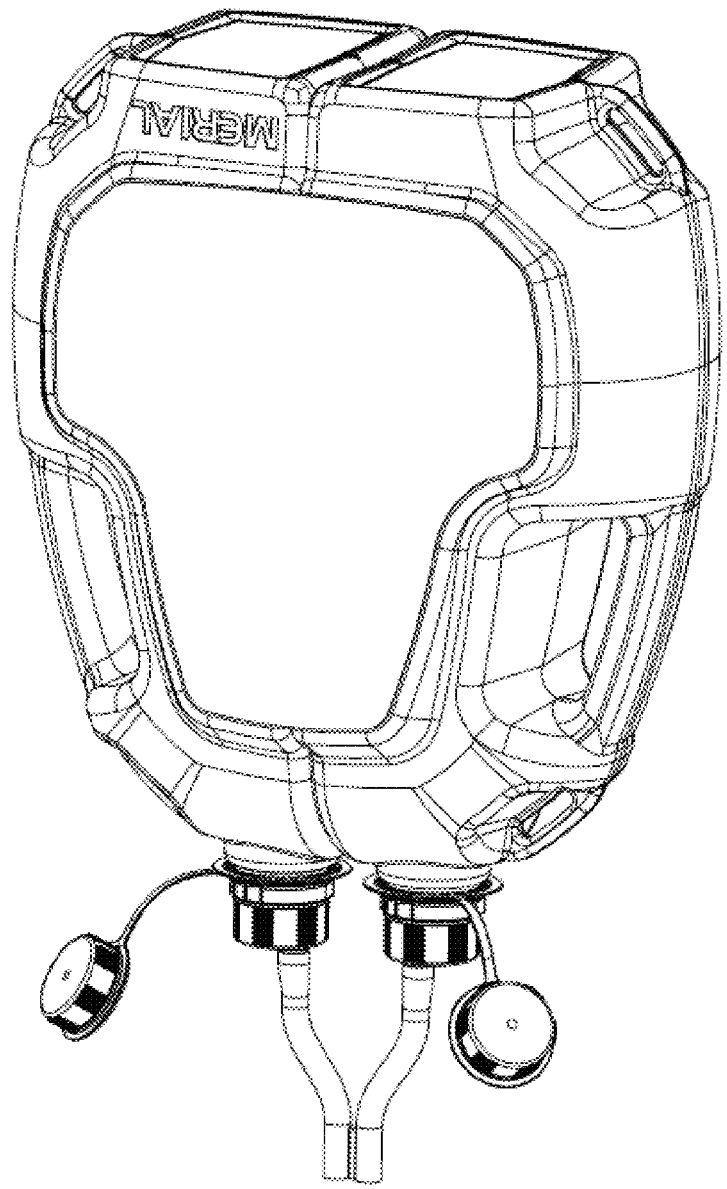
FIG. 10 presents a multi-chamber packaging in its inverted position, shown with two vented draw-off caps and suitable hoses.
Figure 11:
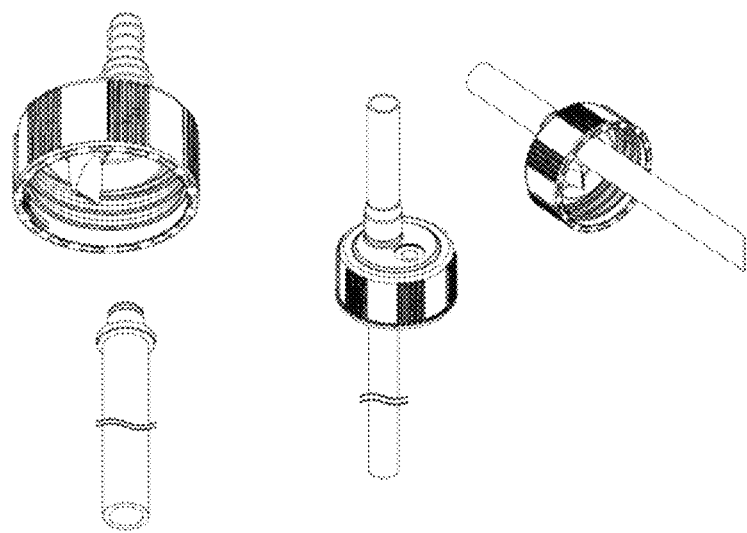
FIG. 11 depicts a dip tube assembly, for use with the packing in it upright position.

In an embodiment, the packaging is used in its upright position, as depicted in FIG. 1. In another embodiment, the packing is used in its inverted position, as depicted in FIG. 10. To use the packaging in it upright position, a user may insert a Dip Tube Assembly (FIG. 11) into the base of the No-Twist Draw-Off Cap. The User may remove the Dip Tube Assembly when using the packaging inverted. The No-Twist Draw-Off Cap and the Dip Tube Assembly may be supplied with the Applicator.

Figure 12:
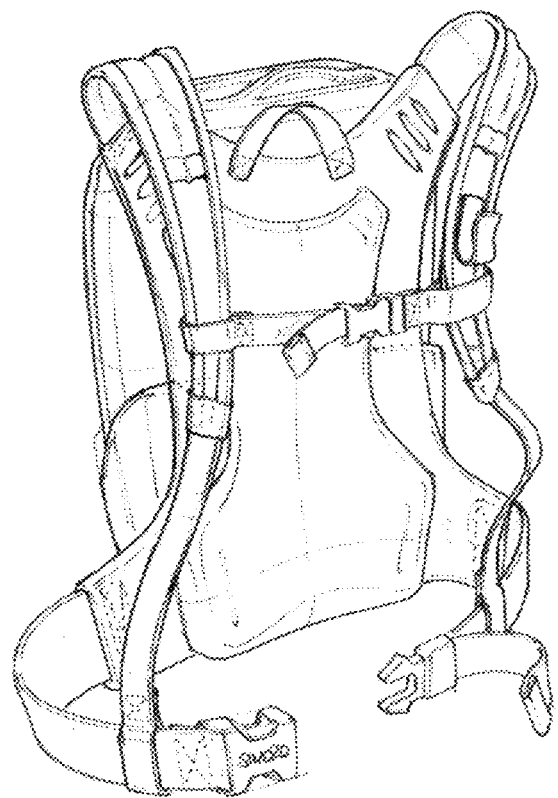
FIG. 12 presents a harness for the multi-chamber packaging.
Figure 13:
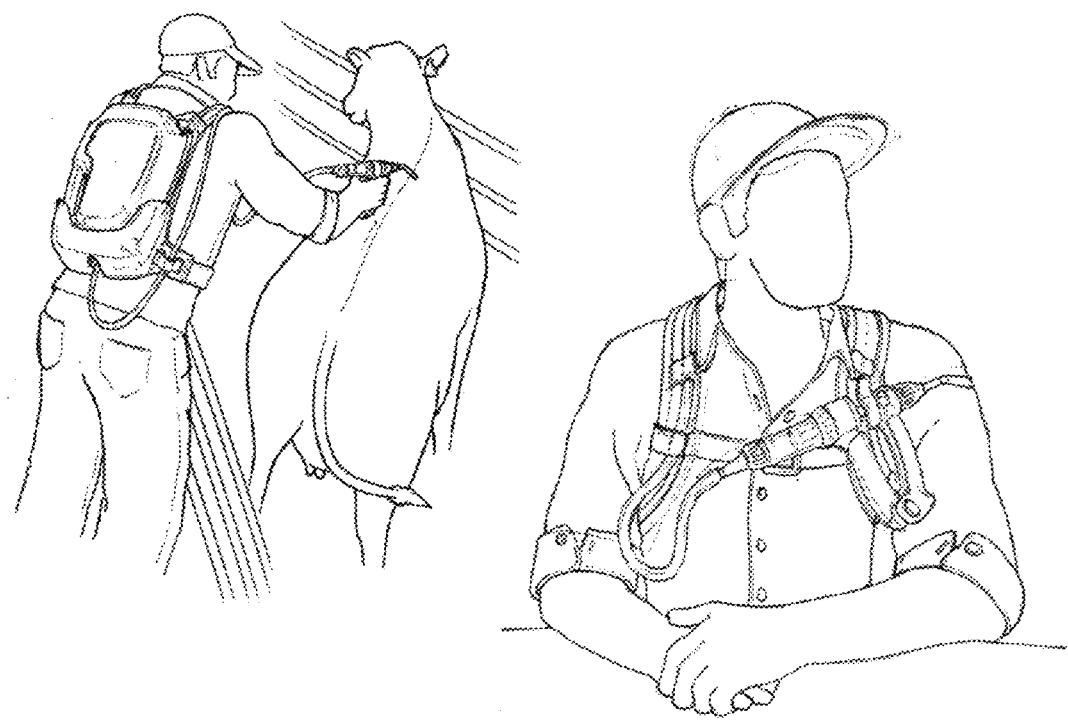
FIG. 13 is a drawing of a person equipped with a multi-chamber, multi-formulation fluid delivery system according to the disclosure.
Figure 14A:
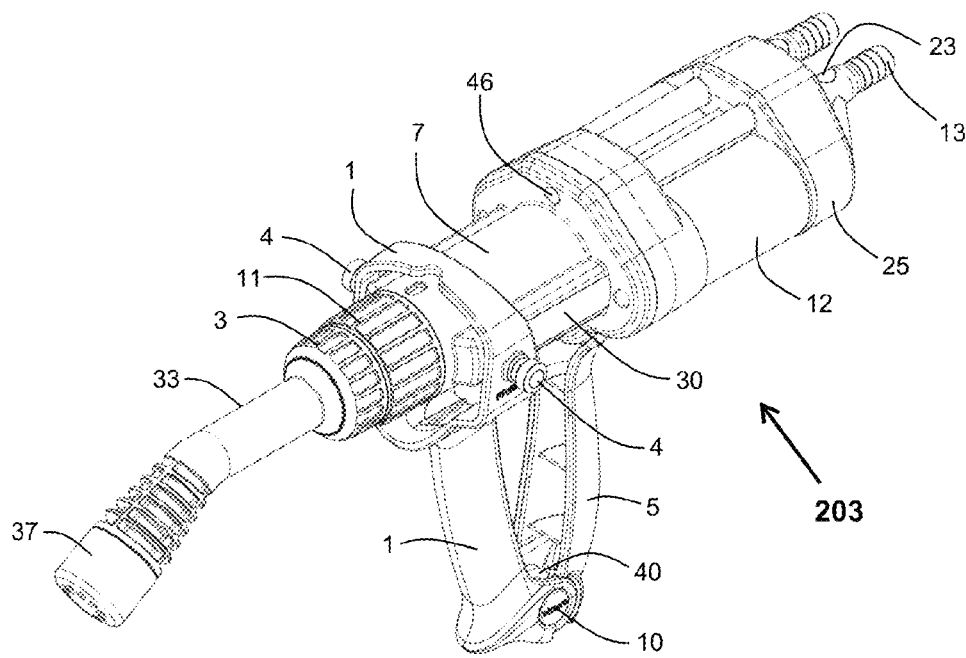
FIG. 14A is a front/right/top view of a multi-chamber applicator (203)
Figure 14B:
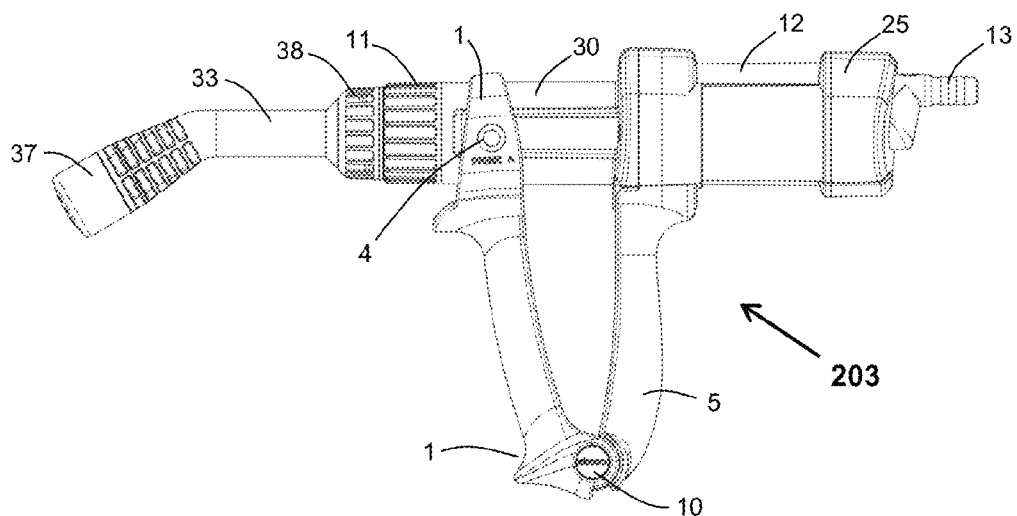
FIG. 14B is a left view of a multi-chamber applicator (203)
Figure 14C:
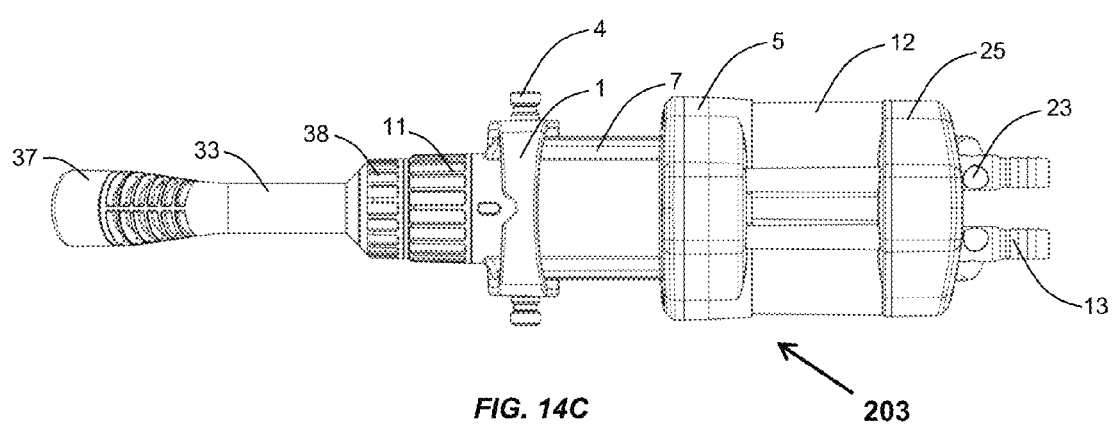
FIG. 14C is a top view of a multi-chamber applicator (203)
Figure 15A:
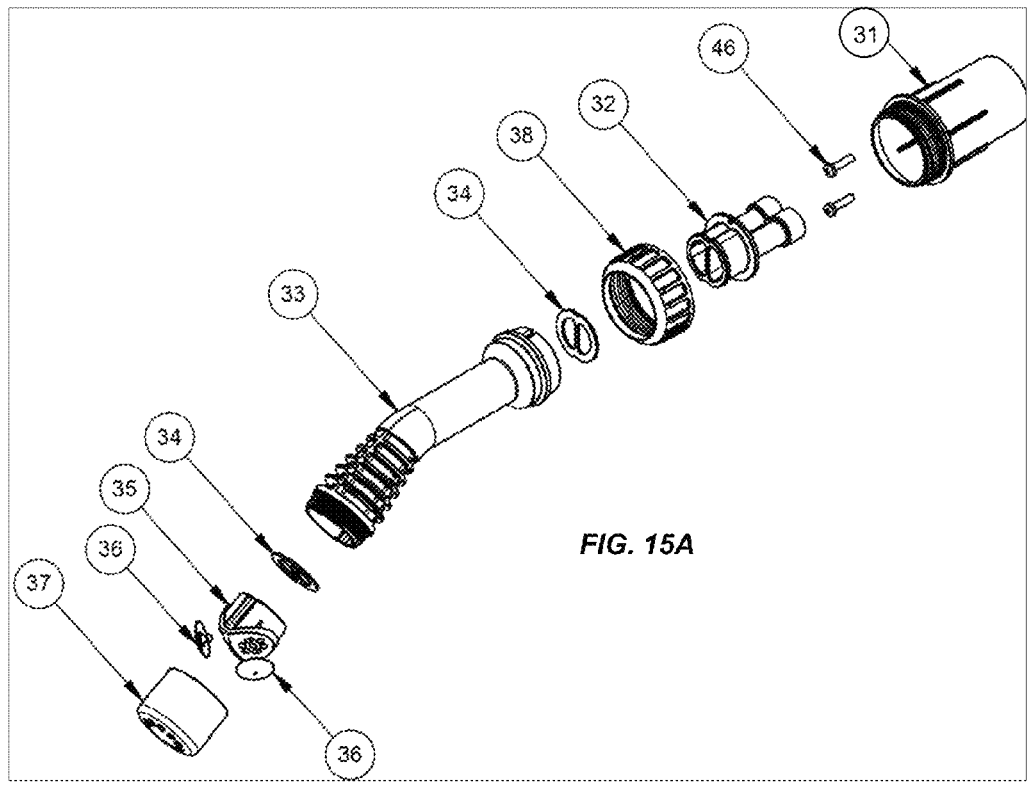
FIG. 15A is an exploded view of a portion of the applicator (203), showing the front-most (i.e. in the direction of the nozzle) of the applicator.
Figure 15B:
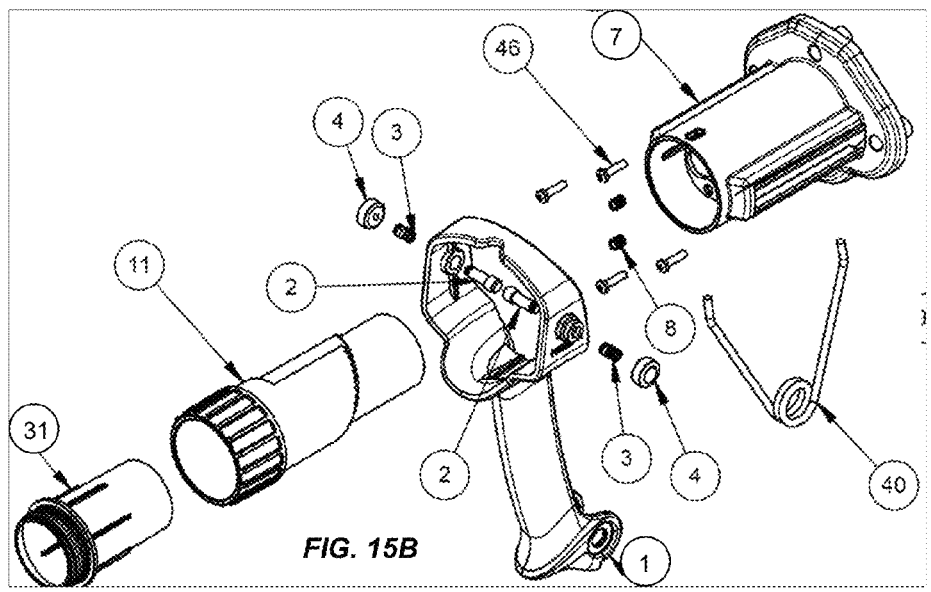
FIG. 15B is an exploded view of a portion of the applicator (203), showing from the front of the nozzle to about the middle of the applicator.
Figure 15C:
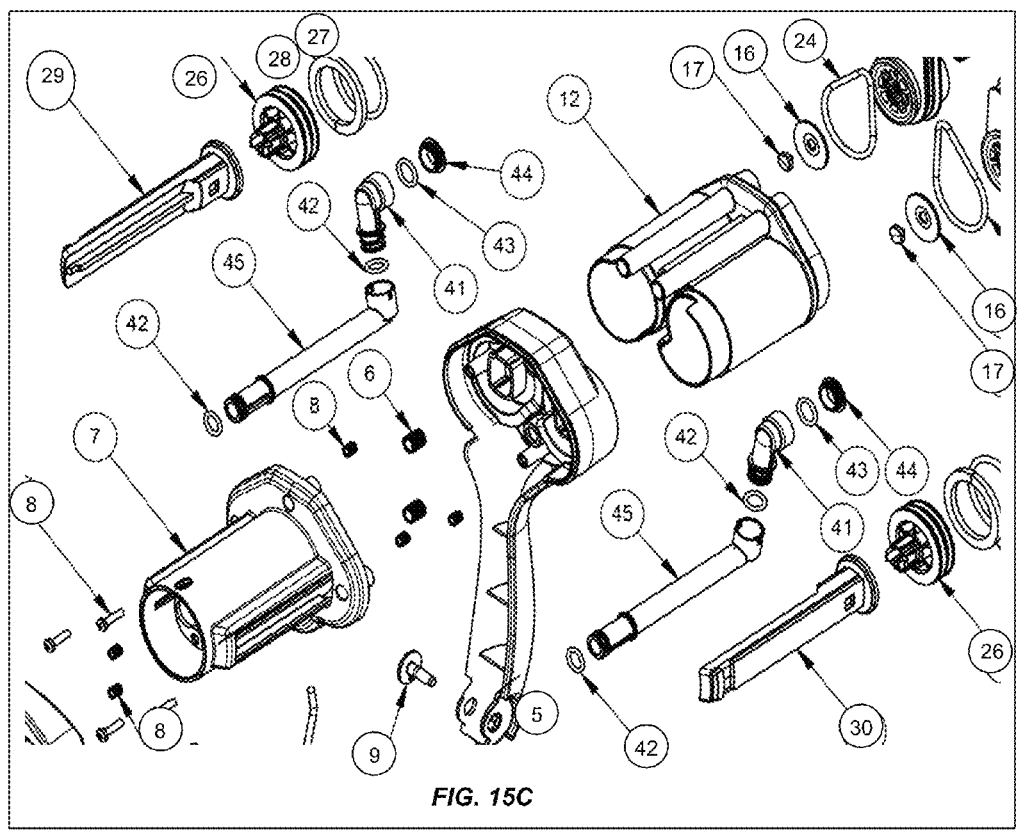
FIG. 15C is an exploded view of a portion of the applicator (203), showing from the middle of the applicator to the housing for the barrels.
Figure 15D:
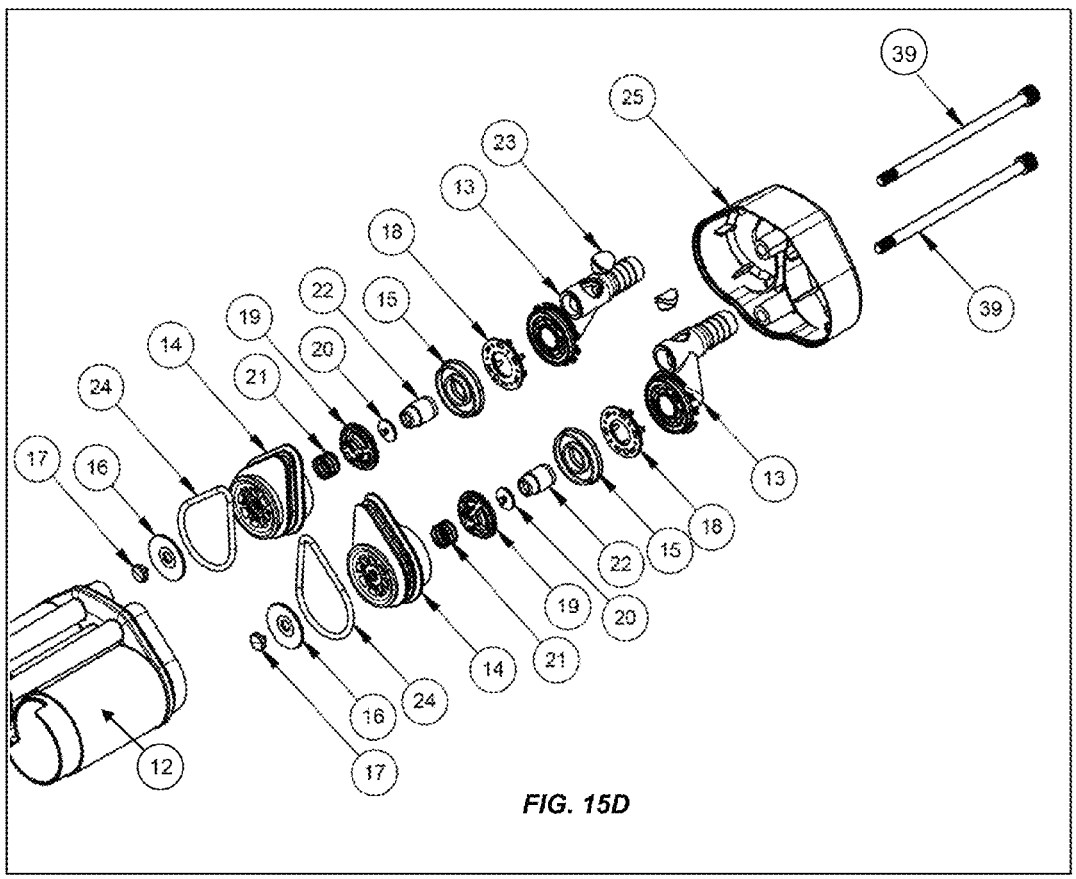
FIG. 15D is an exploded view of a portion of the applicator (203), showing the back-most end.
Figure 16:
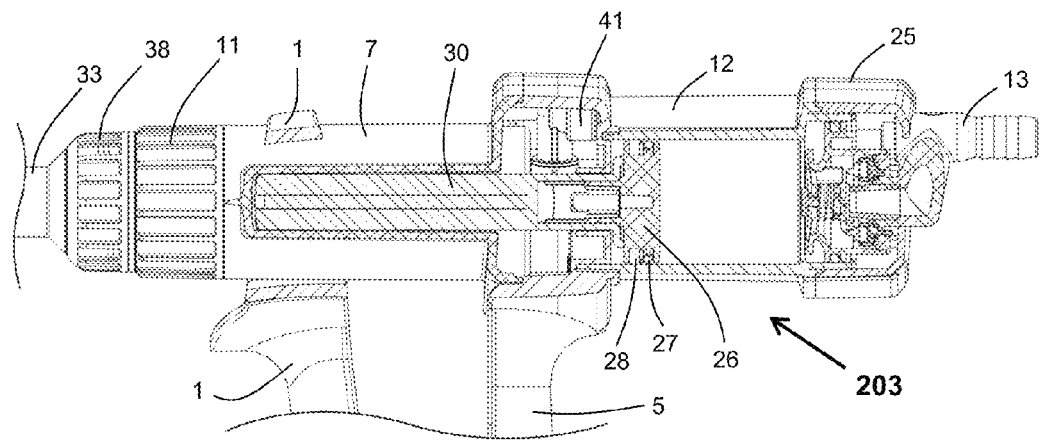
FIG. 16 is a cross-section of the applicator (203)
Figure 17A:
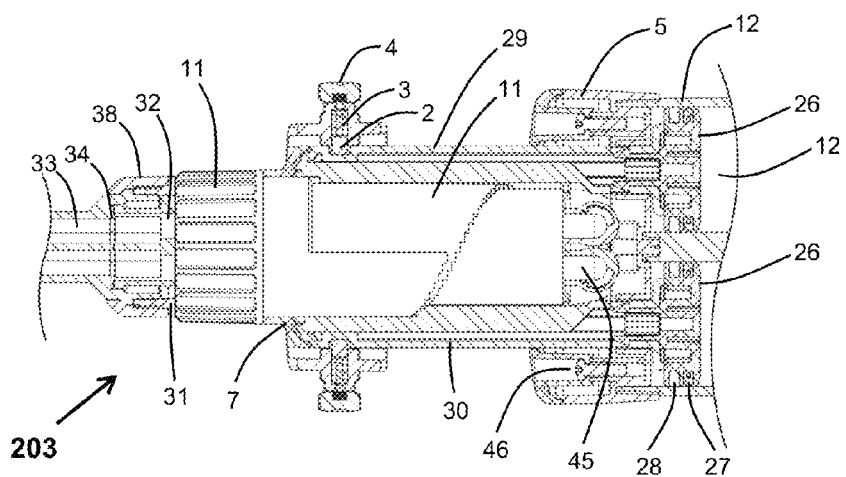
FIG. 17A is a cross-section of the applicator (203), showing the "double staircase" dosage regulator.
Figure 17B:
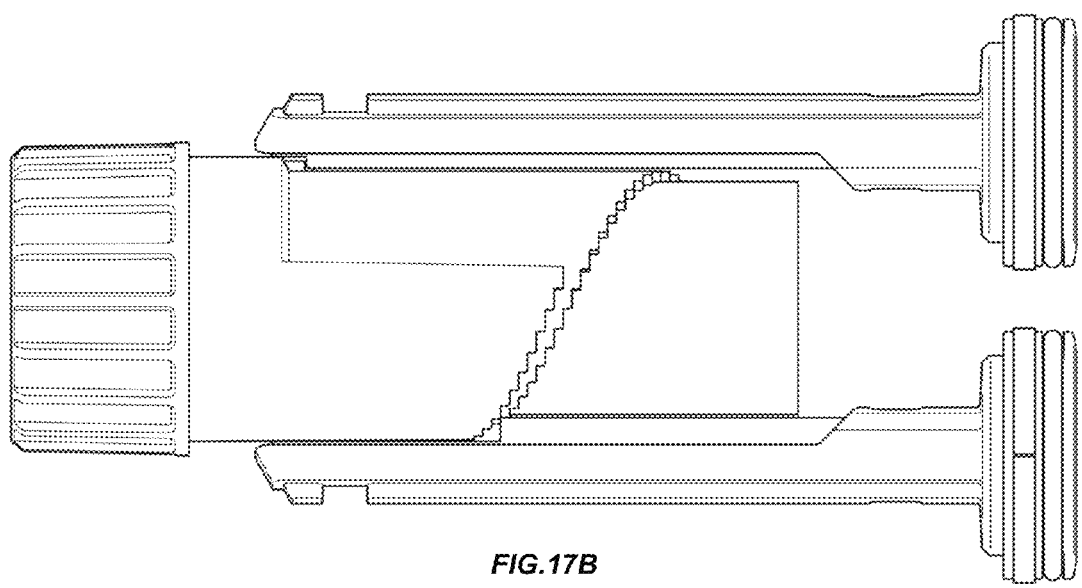
FIG. 17B shows the dosage regulator engaging with the two plungers if the depicted dual-chamber applicator.
Figure 18A:
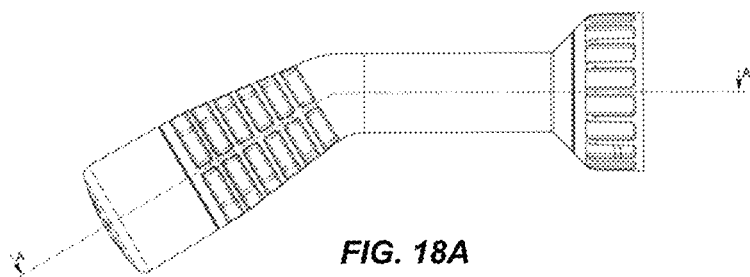
FIG. 18A is a nozzle according to the disclosure, marked with the cross-section line corresponding to the cross-section depicted in FIG. 18B.
Figure 18B:
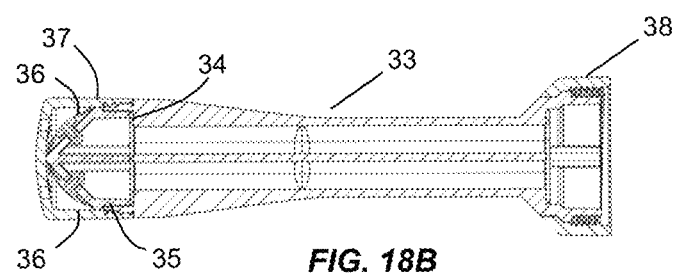
FIG. 18B is the cross-section of the nozzle, which corresponds to the marking in FIG. 18A.
Figure 19A:
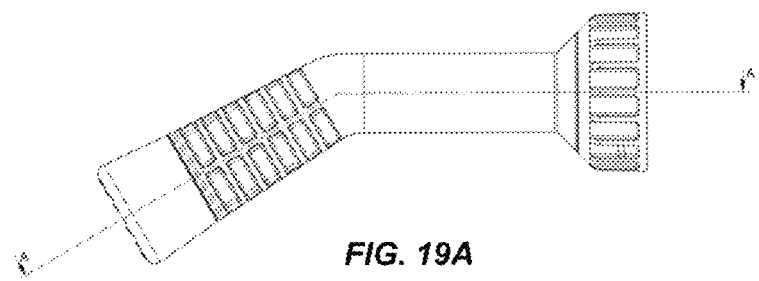
FIG. 19A is an alternate "open rose" nozzle, marked with the cross-section line corresponding to the cross-section depicted in FIG. 19B.
Figure 19B:
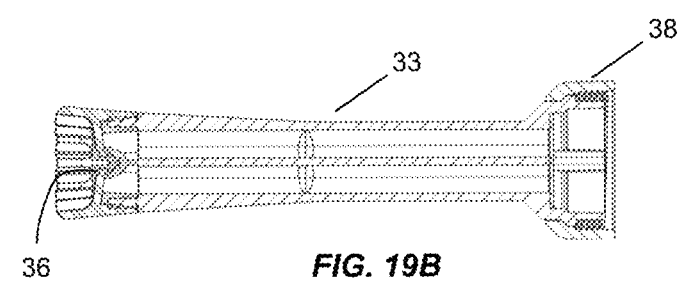
FIG. 19B is the cross-section of the alternate "open rose" nozzle, which corresponds to the marking in FIG. 19A.
Figure 20A:
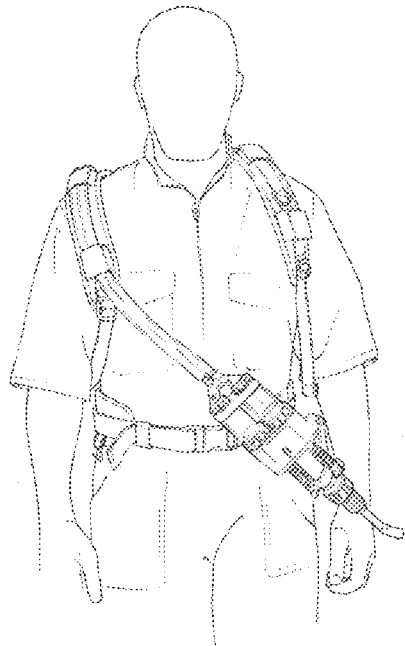
FIG. 20A is a drawing of a user, shown from the front, equipped with the applicator and co-packaging (in the upright position) according to the disclosure.
Figure 20B:
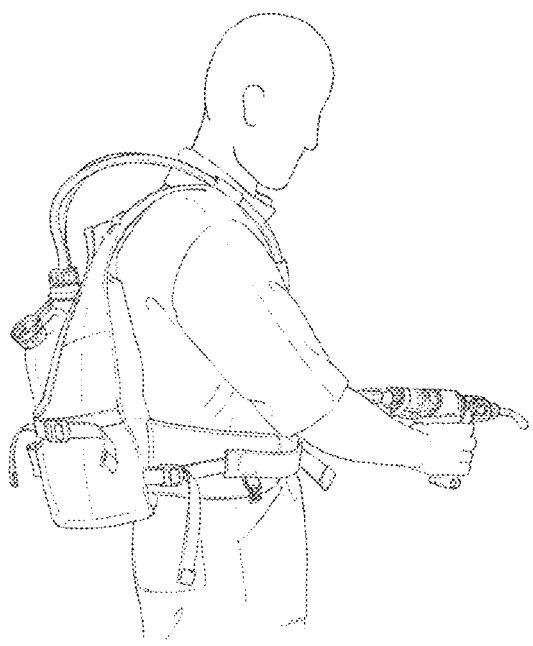
FIG. 20B is a drawing of a user, shown from the right side, equipped with the applicator and co-packaging (in the upright position) according to the disclosure.
Figure 21A:
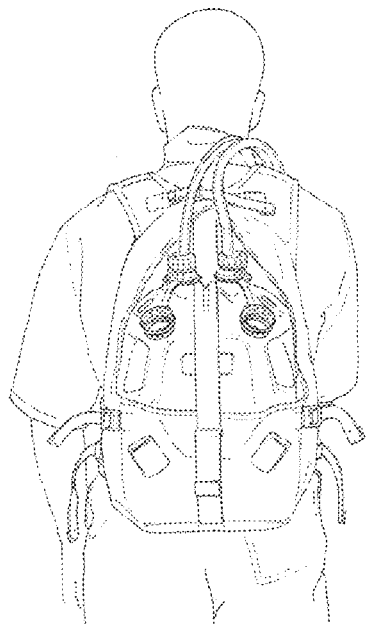
FIG. 21A is a drawing of a user, shown from the back, equipped with the applicator and co-packaging (in the upright position) according to the disclosure.
Figure 21B:
FIG. 21B is a drawing of a user, shown from the back, equipped with the applicator and co-packaging (in the inverted position) according to the disclosure.
Figure 22A:
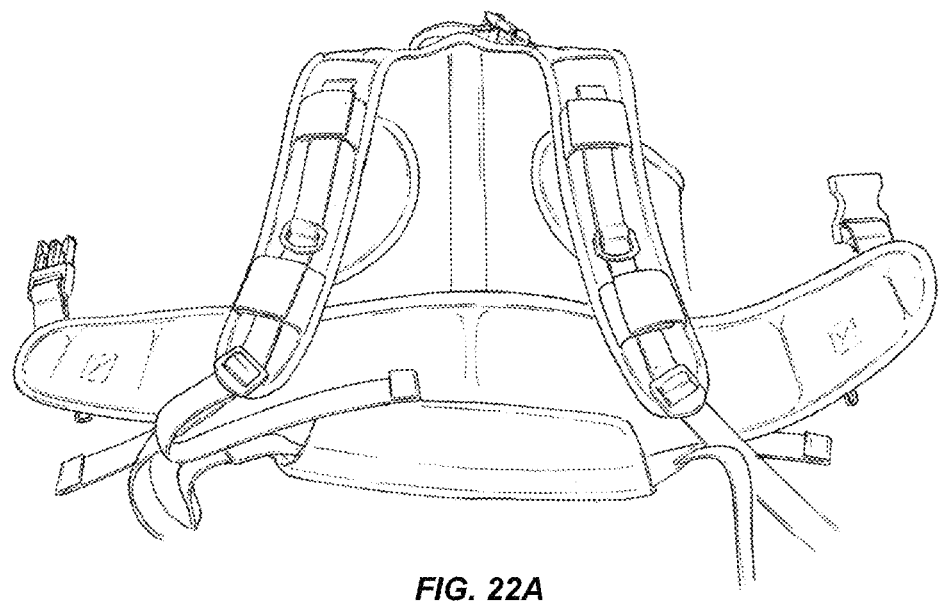
FIG. 22A is a drawing of a harness for the co-packaging, showing the surface that would be in contact with a user's back.
Figure 22B:
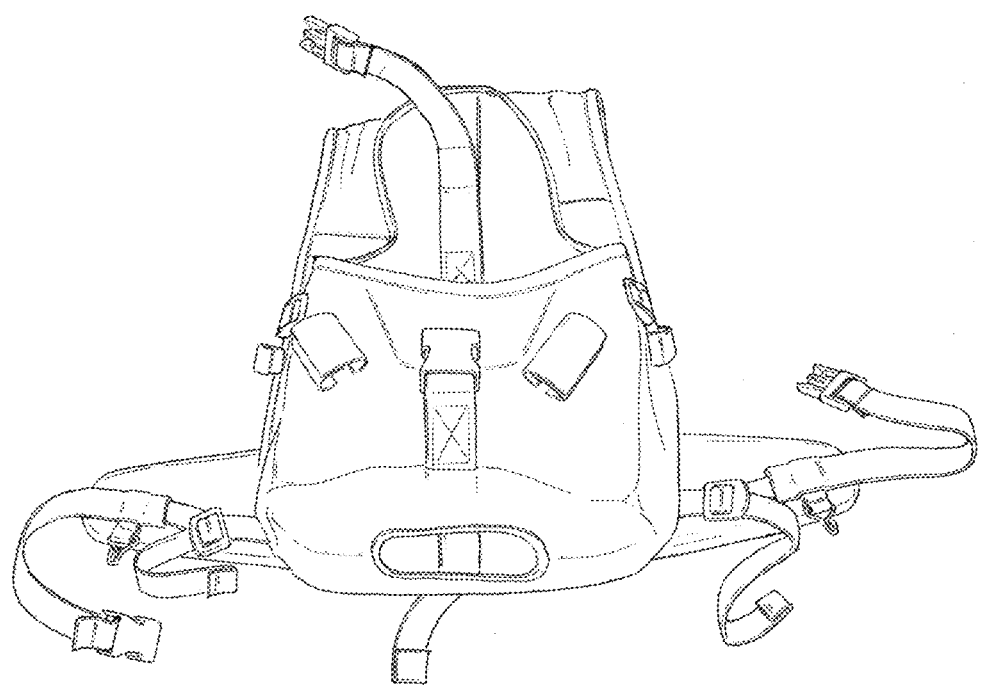
FIG. 22B is a drawing of a harness for the co-packaging, showing the surface that would be visible when viewing a user (equipped therewith) from behind.

In an embodiment, the System includes a harness for the multi-chamber packaging, substantially as depicted in FIG. 12. A back mounted harness may contain single or multi-chamber packaging in the upright or inverted configurations, providing optimum comfort and user convenience.

In a particular embodiment, the harness is designed for use with a 10 L twin co-packaging. In other embodiments, the harness may be used with any other configuration of the multi-chamber packaging.

The harness may accommodate upright or inverted packaging, and it should be quick and intuitive for a user to load or replace the multi-chamber packaging. Optional attachments may include an applicator hook and a pocket for containing, for example, a cell phone or other communication device.

Methods for Simultaneously Delivering Two or More Formulations

As indicated above, many veterinarily important active ingredients are not easily co-formulated, and so must be delivered separately/sequentially. The inability to deliver effective AI simultaneously places a great economic burden upon those wishing to treat large numbers of production animals, including bovines, ovines, and caprines. The System of the present disclosure cuts the time and expense of delivering incompatible active ingredients by more than half, for at least two important reasons. First, a single application will take about half as long as a double application. Second, two separate AI formulations are typically less expensive than the corresponding dual formulation, if such an AI combination is even available. And finally, the development of resistance among parasites and pests has necessitated the used of multiple classes of active ingredients, which all but ensures those who raise animals must incur the expense of multiple formulation applications.

Thus, in a particular embodiment, the invention provides a method for simultaneously delivering at least two formulations, which contain at least one active ingredient that is not stable, soluble, or otherwise compatible with at least one other active ingredient.

In an embodiment, the invention provides a method for simultaneously administering to an animal in need thereof multiple active ingredient formulations comprising the steps of:
a. connecting a multi-chamber applicator to multi-chamber packaging containing, each of its chambers containing a separate formulation;
b. loading or priming the multi-chamber applicator with the separate formulations; and
c. actuating the applicator to dispense the formulations onto or into the animal, thereby administering the active ingredients.

In an embodiment, a first formulation contains at least one active ingredient that cannot easily be co-formulated with at least one of the active ingredients present in a second formulation.

In another embodiment, there is no known stable and effective co-formulation of the active ingredients.

In yet another embodiment, the simultaneous administration provides a stronger or synergistic effect, when compared to the effect achieved when the one or more formulations is administered via separate applications.

In an embodiment of the method, one active ingredient is fipronil and another active ingredient is amitraz. Alternatively, one of the active ingredients may be a macrocyclic lactone, while the other active ingredient is levamisole or fluazuron. Many combinations will be appreciated by those skilled in the art of formulating active ingredients for veterinary and pharmaceutical applications. Thus, applicants envision that any combination of active ingredients that has been recalcitrant to co-formulation may be more effectively and simultaneously applied (as separate formulations) using the System of the instant disclosure. In a particular embodiment of the method, the simultaneous administration of fipronil and amitraz has a stronger or synergistic pesticidal effect as compared to a separate administration of fipronil and amitraz.

In another embodiment, the stronger effect is extended duration of efficacy against acarids, more rapid killing efficacy against acarids, reduced development of pesticide resistance, or any combination thereof.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Where in the foregoing description, reference has been made to specific components or integers of the invention having known equivalents, then such equivalents are herein incorporated as if individually set forth.

EXAMPLES

Example 1

Figure 3B:
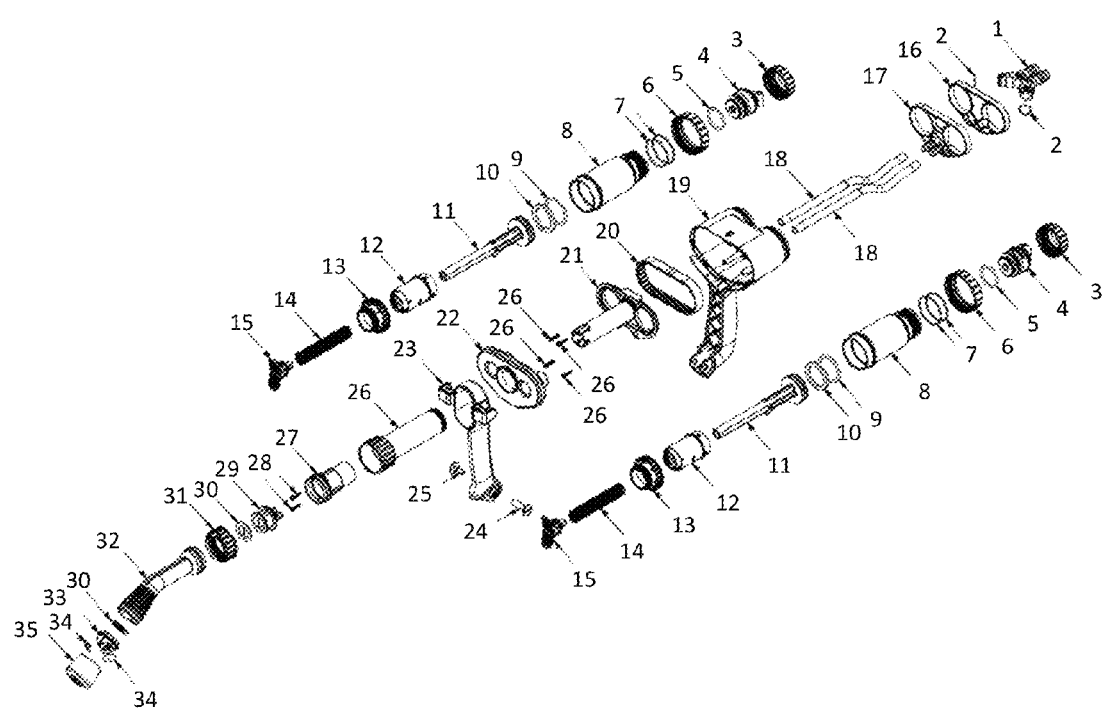
FIG. 3B is an exploded view of the applicator.
Figure 3C:
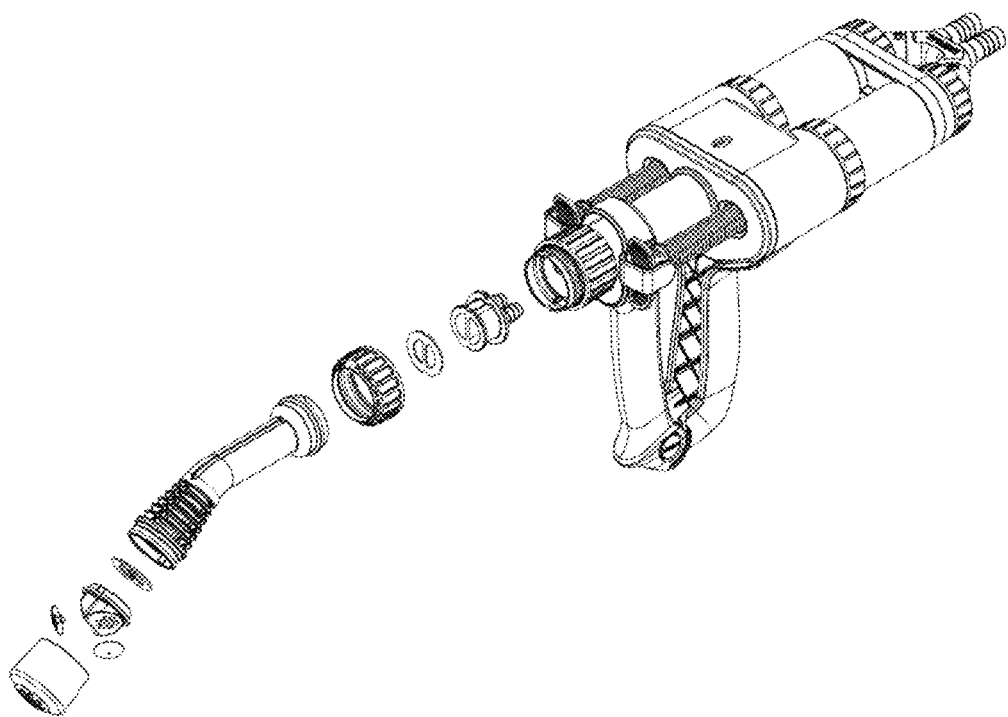
FIG. 3C is an exploded view of the nozzle of the applicator.
Figure 3D:
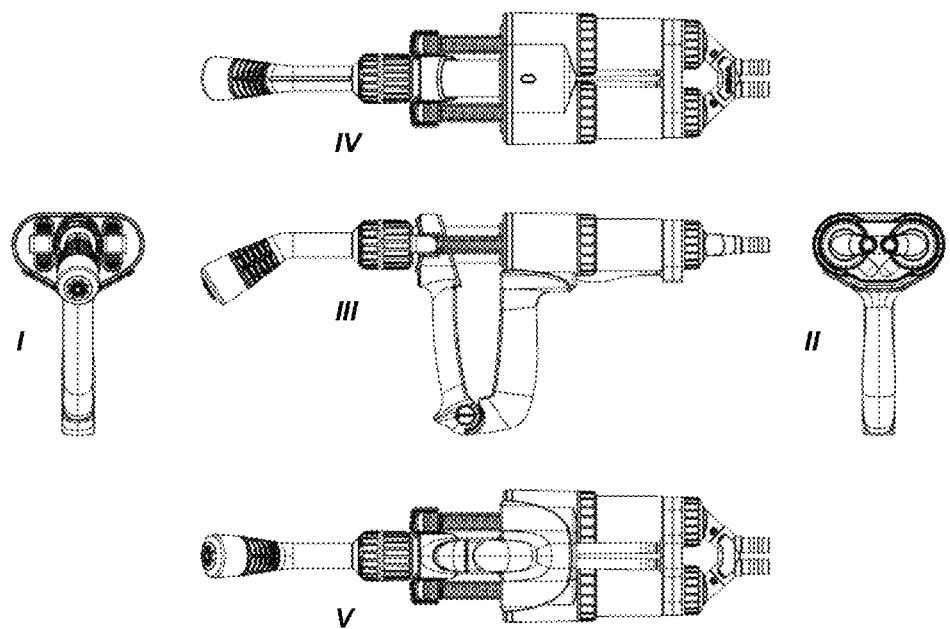
FIG. 3D contains multiple views of the applicator: front (I); back (II); left side (III); top (IV); and bottom (V)
Figure 3E:
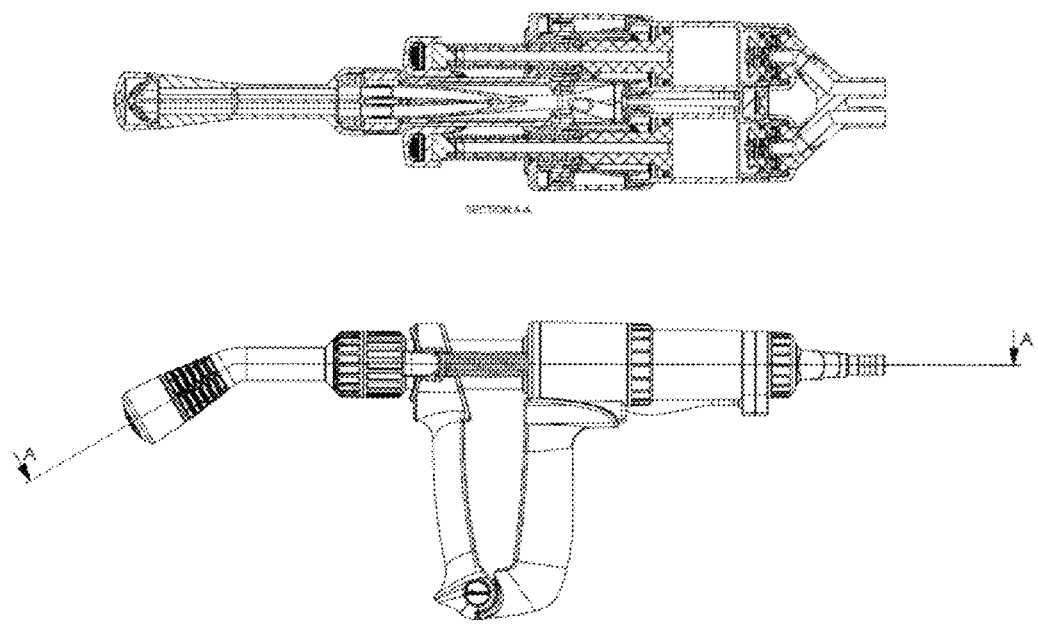
FIG. 3E shows a top-bottom cross-section of the applicator (location of the section is marked in the accompanying left side view)
Figure 3F:
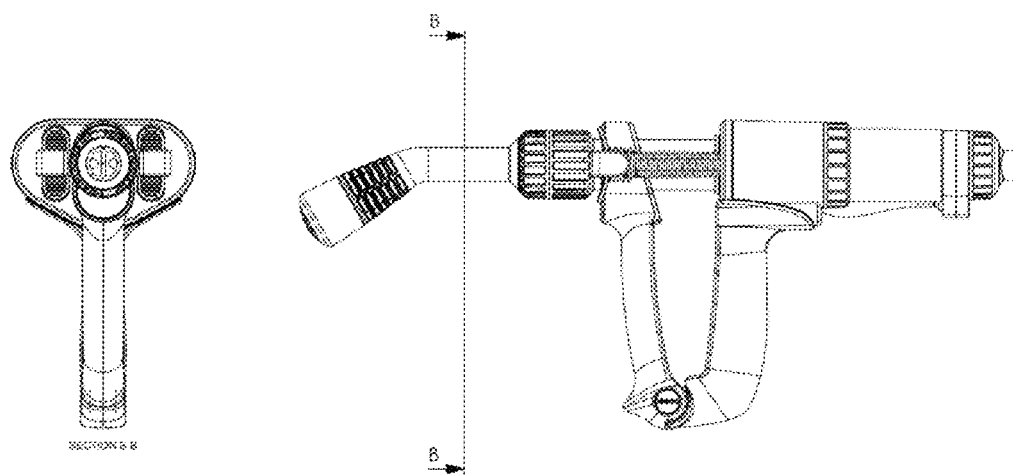
FIG. 3F shows a front-back cross-section of the applicator (location of the section is marked in the accompanying left side view)
Figure 4:
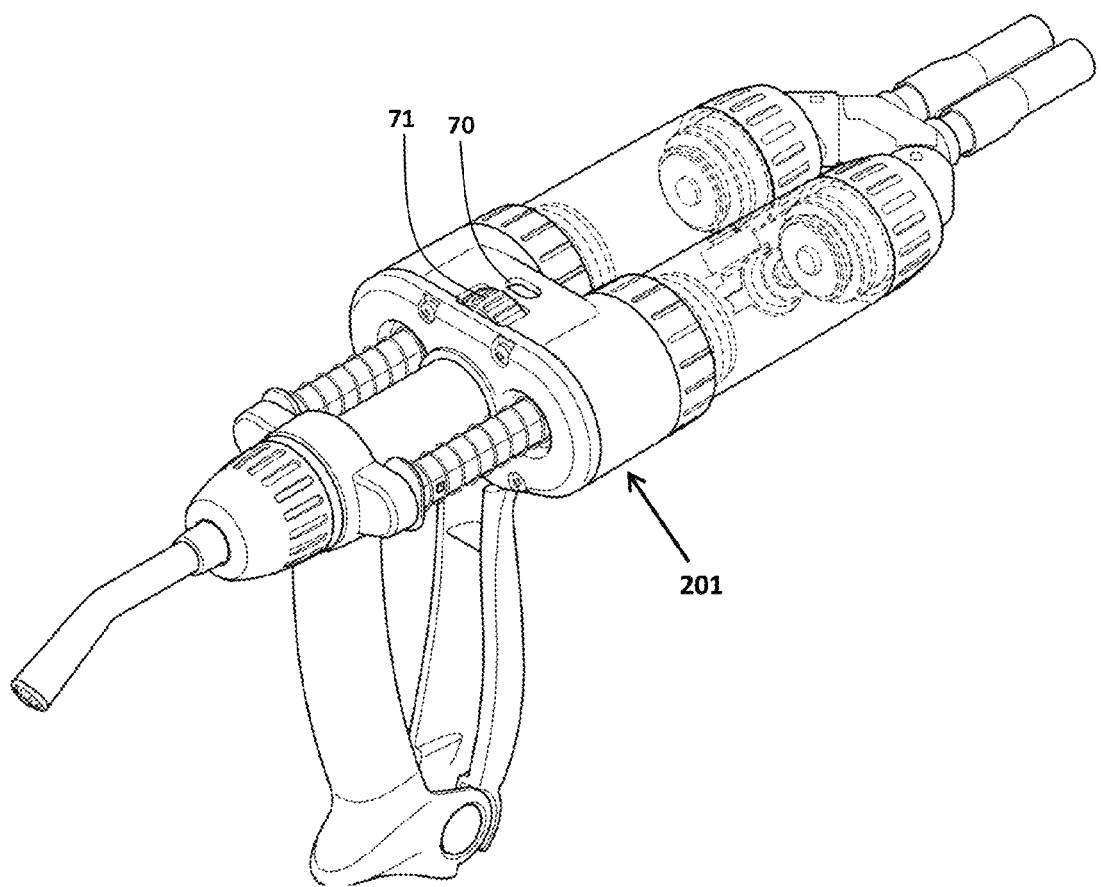
FIG. 4 depicts an alternate embodiment of an applicator (201) according to the invention, wherein the dosage selector (71) immediately adjacent to the dosage indicator (70), instead of as depicted in FIG. 3A, where the dosage selector (71) circumscribes the central cylinder (76)

In an embodiment, the applicator comprises the parts as shown in FIG. 3B, and as recited in Table 1 below.

TABLE 1

Constituent components of the Applicator (200) depicted in FIG. 3B. The numbering of the components applies only to this embodiment (i.e. applicator 200), unless otherwise expressly stated.

| FIG. 3A Number | Quantity | Description |
| --- | --- | --- |
| 1 | 1 | Delivery Tube Connector |
| 2 | 2 | O-Ring |
| 3 | 2 | Inlet Nut |
| 4 | 2 | BREAZE ™ Inlet Assembly |
| 5 | 2 | O-Ring |
| 6 | 2 | Barrel Nut |
| 7 | 4 | O-Ring |
| 8 | 2 | Barrel |
| 9 | 2 | O-Ring |
| 10 | 2 | Felt Washer |
| 11 | 2 | Plunger |
| 12 | 2 | Volume Control |
| 13 | 2 | Toothed Wheel |
| 14 | 2 | Plunger Spring |
| 15 | 2 | Plunger Latch |
| 16 | 1 | Outlet Manifold (Rear Half) |
| 17 | 1 | Outlet Manifold (Front Half) |

TABLE 1-continued

Constituent components of the Applicator (200) depicted in FIG. 3B. The numbering of the components applies only to this embodiment (i.e. applicator 200), unless otherwise expressly stated.

| FIG. 3A Number | Quantity | Description |
| --- | --- | --- |
| 18 | 2 | Outlet Tube |
| 19 | 1 | Rear Handle |
| 20 | 1 | Dose Display Belt |
| 21 | 1 | Outlet Support |
| 22 | 1 | Cover |
| 23 | 1 | Front Handle |
| 24 | 1 | Female Pivot Pin |
| 25 | 1 | Male Pivot Pin |
| 26 | 1 | Dose Adjuster |
| 27 | 1 | Outlet Adapter |
| 28 | 6 | Screw |
| 29 | 1 | Outlet Tube Connector |
| 30 | 2 | Gasket |
| 31 | 1 | Nozzle Nut |
| 32 | 1 | Dual Chamber Nozzle |
| 33 | 1 | Outlet Valve Seat |
| 34 | 2 | Outlet Valve |
| 35 | 1 | Nozzle Tip |

Accordingly, an applicator according to the disclosure may comprise the following: Delivery Tube Connector (1), O-Ring (2), Inlet Nut (3), BREAZE™ Inlet Assembly (4), O-Ring (5), Barrel Nut (6), O-Ring (7), Barrel (8), O-Ring (9), Felt Washer (10), Plunger (11), Volume Control (12), Toothed Wheel (13), Plunger Spring (14), Plunger Latch (15), Outlet Manifold (Rear Half) (16), Outlet Manifold (Front Half) (17), Outlet Tube (18), Rear Handle (19), Dose Display Belt (20), Outlet Support (21), Cover (22), Front Handle (23), Female Pivot Pin (24), Male Pivot Pin (25), Dose Adjuster (26), Outlet Adapter (27), Screw (28), Outlet Tube Connector (29), Gasket (30), Nozzle Nut (31), Dual Chamber Nozzle (32), Outlet Valve Seat (33), Outlet Valve (34), Nozzle Tip (35), In a particular embodiment, all the parts are connected as indicated in FIGS. 3A-E.

Now that the disclosure has been made, the inventors envision that the applicator (200) may comprise all the above-recited parts (1-35), or any combination thereof, including any obvious equivalents thereof, provided that the applicator functions in substantially the same way as the applicator depicted in FIGS. 14A-C and 15A-D.

Example 2

In an embodiment, the applicator (203) comprises the parts as shown in FIG. 15A-D, and as recited in Table 2 below. The numbering of the components applies only to this embodiment (i.e. applicator 203), unless otherwise expressly stated.

TABLE 2

Constituent components of the Applicator (203) depicted, for example, in FIGS. 14A-C and 15A-D.

| FIG. 15A-D | Part Name | Description |
|---|---|---|
| 1 | Front handle | Squeeze to discharge. |
| 2 | Plunger engagement pin | Normally the pin is engaged with the vertical slot near the front of the corresponding plunger shaft (29, 30). Pulling the knob out disengages that plunger for one squeeze. This allows the opposite side to be primed further without discharging fluid unnecessarily from the disengaged side. The spring (3) causes the pin to automatically re-engage the plunger shaft when the front handle (1) returns to its forward position. |
| 3 | Spring | |
| 4 | Knob | |
| 5 | Rear handle | This is the "fixed handle" for the applicator. In practice, both the front and rear handles move towards one another when the handles are squeezed. The rear handle may move less than does the front handle. |
| 6 | Thread insert | These metal components screw into the plastic rear handle (5) to provide anchor points for the tie rods (39). |
| 7 | Housing | This is attached to the rear handle (5) by the four screws (46). It guides the plunger shafts (29, 30) and the volume control (11). It provides structural support for the nozzle assembly.<br>The housing (7) may also be integral with the rear handle (5), as one molded part. |
| 8 | Thread insert | These metal components screw into the plastic rear handle (5) to provide anchor points for the screws (46). |
| 9 | Pivot pin (male) | These pins provide the pivot point between the front and rear handles (1, 5). |
| 10 | Pivot pin (female) | |
| 11 | Volume control, or Dose adjuster | The ribs at the front provide a grip for turning the volume control/dose adjuster. Text (not shown) giving the dose size in mL is printed around the component (where the arrowhead is positioned on the drawing). This text is visible through the small window on the top front of the housing (7).<br>The volume control has two spiral staircases wrapped around its outer surface. These staircases are positioned at different diameters, and offset slightly axially. The inner (and slightly rearward) staircase engages with a rib on the left-hand plunger shaft (30), limiting how far forward this plunger shaft can travel. The outer (and slightly forward) staircase engages with a rib on the right-hand plunger shaft (29), limiting how far forward this plunger shaft can travel.<br>The ribs on the plunger shafts (29, 30) extend radially inwards by different lengths, determining which spiral staircase each of them engages with. The axial positions of these ribs on the plunger shafts also differ between the left and right plunger shafts (29, 30). The rib positions are such that the two plunger shafts (29, 30) have the same axial position when in their forward position against the spiral staircases, despite engaging with opposite sides of the volume control (11).<br>Note that it may be generally necessary to squeeze the handles (1, 5), moving the plunger shafts (29, 30) rearwards, before rotating the volume control (11) in order to change the dose setting. |
| 12 | Barrel component | Transparent. This forms the two chambers (barrels) for pumping the fluid. The one molding integrates the left- and right-hand barrels, the outlet tubes (on top) for carrying the fluid forward towards the nozzle, and two guide tubes for the tie rods (39) that hold the assembly together.<br>When the barrel component (12) is engaged with the rear handle (5), the outlet tubes engage with the two elbow connectors (41). |
| 13 | Fluid inlet | These components make up the BREAZE ™ valve assembly. |
| 14 | BREAZE ™ valve housing | In the instantly depicted DUAL- BREAZE ™ version, the fluid inlet (13) is equivalent to the plunger shaft of the original technology disclosure (i.e. single-chamber dosage device), but is now fixed in place. The hose barbs at its rear end may be removed and replaced by snap-fit connectors, as desired.<br>The BREAZE ™ valve housing (14) replaces the plunger head of the original single chamber BREAZE ™ delivery device. It has a tear-drop shaped flange that seals into the barrel (12) with fixed O-ring seal (24). This tear-drop shape allows fluid to be directed to the fluid outlet tubes that are integral with the top of the barrel (12). |
| 15 | Diaphragm | |
| 16 | Inlet valve | |
| 17 | Inlet valve retention pin | |
| 18 | Clamp ring | |
| 19 | Follower | |
| 20 | Jumper washer | |
| 21 | Spring | |
| 22 | Jet | |
| 23 | Plug | Required to plug the hole in the side of the fluid inlet (13). |
| 24 | O-ring seal | |
| 25 | Rear cover | Holds the fluid inlets (13), the BREAZE ™ valve assemblies and the barrel in place (using the tie rods (39)). |
| 26 | Plunger head | In an embodiment, the connection between the plunger head (26) and the plunger shaft (29, 30) may be self-aligning. That is to say, they would move together axially, but the plunger head (26) would be free to move slightly in a lateral plane. This would allow it to self-align with the barrel bore, without any side loads from the plunger shaft endangering its seal with the barrel wall. Such self-alignment is envisioned by the current disclosure, and would serve to accommodate manufacturing tolerances. |

TABLE 2-continued

Constituent components of the Applicator (203) depicted, for example, in FIGS. 14A-C and 15A-D.

| FIG. 15A-D | Part Name | Description |
|---|---|---|
| 27 | Plunger O-ring | Seals the plunger head (26) to the wall of the barrel (12). This is a sliding seal. |
| 28 | Felt washer | Soaked in oil to lubricate the bore of the barrel (12) with each stroke. |
| 29 | Plunger shaft (right hand side) | The plunger shafts (29, 30) slide inside the housing (7); one on each side. The vertical groove near the front of the plunger shaft (29, 30) engages with the plunger engagement pin (2), so that the plunger shaft is moved by the front handle (1). |
| 30 | Plunger shaft (left hand side) | The part of the plunger shaft in front of the vertical groove should protrude farther outwards than is shown. This is to prevent the plunger engagement pin (2) from moving forward of the vertical groove, even when the pin is in the retracted position. The plunger engagement pin (2) can be retracted and then slide back along the side of the plunger shaft (29, 30), but not forward of it. The two plunger shafts (29, 30) are not identical. The inwardly protruding ribs that engage with the volume control (11) are different lengths radially and in different positions longitudinally. This is to ensure that each engages with the correct spiral on the volume control (11), and both plunger shafts (29, 30) stop in the same longitudinal position despite engaging with opposite sides of the volume control (11). |
| 31 | Outlet adaptor | Connects the nozzle assembly structurally to the housing (7), by means of screws (46). |
| 32 | Outlet tube connector | The back end of the outlet tube connector (32) receives the two outlet tubes (45). The front end seals to the nozzle (33) by means of one of the gaskets (34). |
| 33 | Nozzle | The nozzle has a vertical wall down its center, maintaining separation of the two fluid paths. |
| 34 | Gaskets (multiple places) | For sealing joints. |
| 35 | Outlet valve seat | The outlet valve seat (35) supports the two umbrella valves (36). The valve mounting surfaces are each on a 45° angle to reduce the overall size of the nozzle. Fluid behind the valves is kept separated between the left- and right-hand sides of the applicator. Fluid in front of the valves is allowed to mix. |
| 36 | Umbrella valves | Flexible silicone umbrella valves. These open at a relatively low fluid pressure, in order to minimize the hand squeeze force required. These easy-opening valves are permissible because the BREAZE ™ valve assemblies at the applicator inlet block any excess fluid pressure that is present in the supply hoses. |
| 37 | Nozzle rose | This is, essentially, a shower head. It has a circle of holes. |
| 38 | Nut | Holds the nozzle (33) onto the outlet adaptor (31). |
| 39 | Tie rods | These are long screws extending from the cover (25), through the barrel (12) (between the two halves) and into the rear handle (5). |
| 40 | Handle spring | This steel torsion spring pushes the front handle (1) away from the rear handle (5). The spring coils are in the vicinity of the pivot pins (9, 10) at the base of the handles. The handle spring (40) returns the plungers to the forward position, refilling the barrels with fluid for the next cycle. |
| 41 | Elbow adaptor | This carries the fluid from the outlet tubes that are integral with the top of the barrel (12), down to the outlet tubes (45) that are close to the centerline of the applicator. |
| 42 | O-ring seal (multiple places) | |
| 43 | O-ring seal | |
| 44 | O-ring retainer | Holds the O-ring seal (43) in place in the elbow adaptor (41). This allows the barrel (12) to be readily removed for re-lubrication of the felt washer (28). |
| 45 | Outlet tube | This carries the fluid from the elbow adaptor (41) forward to the outlet tube connector (32) near the nozzle (33). It passes through the inside of the volume control (11) and the housing (7). |
| 46 | Screws (multiple places) | |

Accordingly, an applicator (203) according to the disclosure may comprise the following: a front handle (1), a plunger engagement pin (2), a spring (3), a knob (4), a rear handle (5), a thread insert (6), a housing (7), a thread insert (8), a pivot pin (male) (9), a pivot pin (female) (10), a volume control or Dose adjuster (11), a barrel component (12), a fluid inlet (13), a BREAZE™ valve housing (14), a diaphragm (15), an inlet valve (16), an inlet valve retention pin (17), a clamp ring (18), a follower (19), a jumper washer (20), a spring (21), a jet (22), a plug (23), an O-ring seal (24), a rear cover (25), a plunger head (26), a plunger O-ring (27), a felt washer (28), a plunger shaft (right hand side) (29), a plunger shaft (left hand side) (30), an outlet adaptor (31), an outlet tube connector (32), a nozzle (33), gaskets (34), an outlet valve seat (35), an umbrella valves (36), a nozzle rose (37), a nut (38), tie rods (39), a handle spring (40), an elbow adaptor (41), an O-ring seal (42), an O-ring seal (43), an O-ring retainer (44), an outlet tube (45), and screws (46).

In a particular embodiment, the parts are arranged according to FIGS. 15A-15D. In a particular embodiment, all the parts are connected as indicated in FIGS. 15A-D.

Now that the disclosure has been made, the inventors envision that the applicator (203) may comprise all the above-recited parts (1-46), or any combination thereof, including any obvious equivalents thereof, provided that the applicator functions in substantially the same way as the applicator depicted in FIGS. 14A-C and 15A-D.

Example 3. Anti-Counterfeiting Measures

Figure 23A:
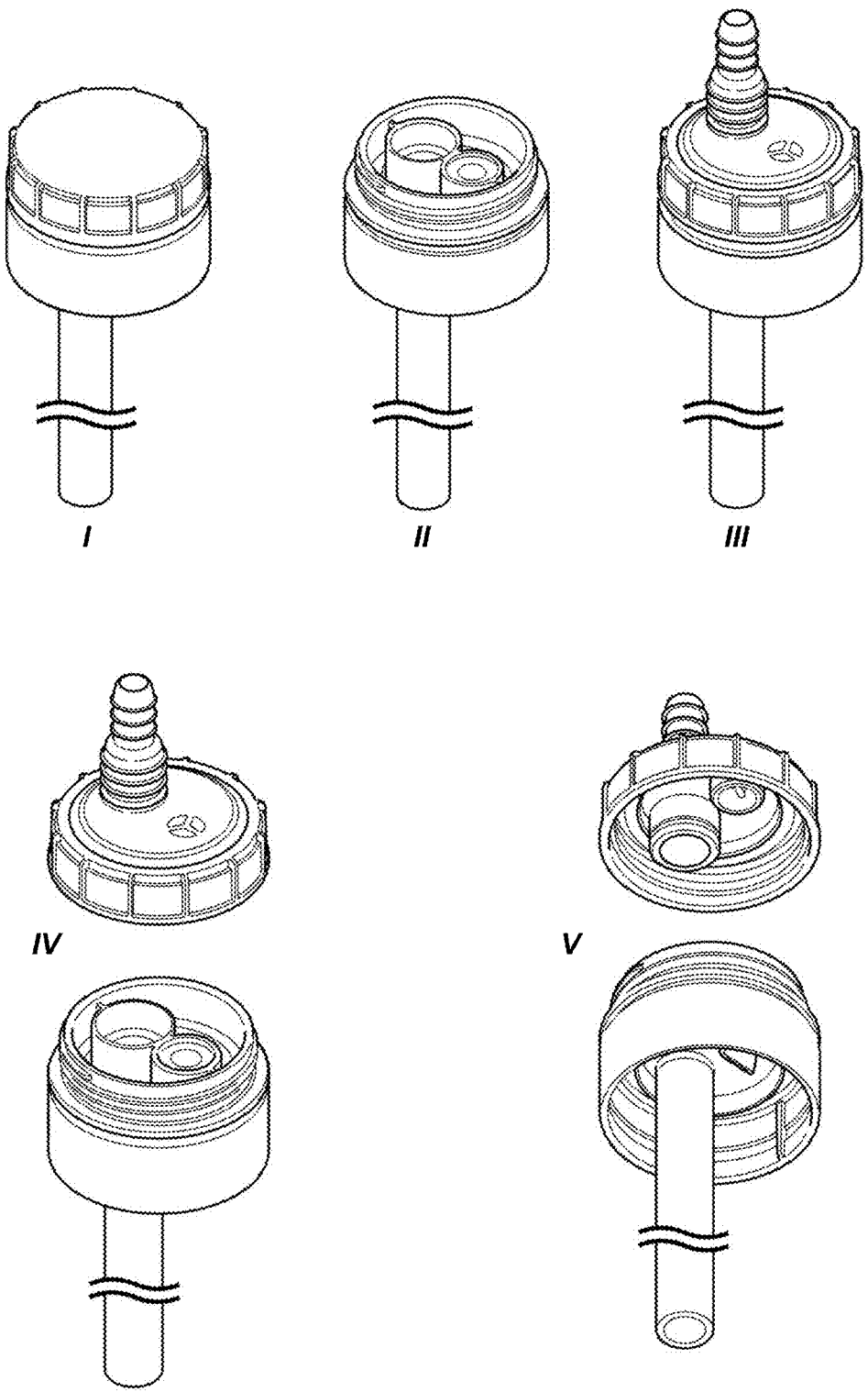
FIG. 23A depicts vented caps and anti-counterfeiting measures according to the disclosure.
Figure 23B:
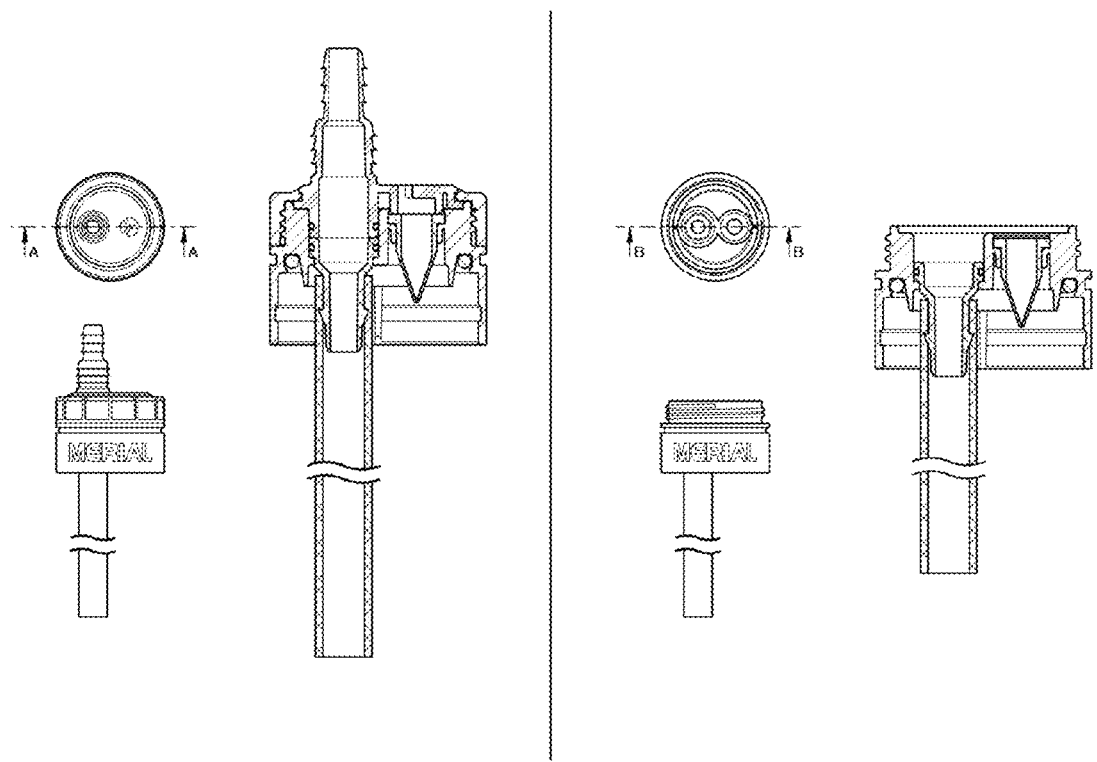
FIG. 23B depicts cross-sections of vented caps and anti-counterfeiting measures according to the disclosure.

In an embodiment, the red part (shown as dark grey in FIG. 23A-B) snaps onto the bottle at the filling plant and cannot be easily removed. The long dip tube (semi-rigid) may be supplied separately. If the user wishes to use the bottle inverted, then the dip tube is not used. For use with the bottle in the upright position, the user pushes the dip tube in through the hole in the red (dark grey in FIG. 23A-B) cap, until it's in the position shown in the pictures. It is not necessary to remove the red cap. The dip tube cannot be removed once it has been fitted. The red (dark grey) cap includes a one-way air breather valve. This admits air to the bottle when the fluid is withdrawn. The valve prevents fluid leaking out the vent if the bottle is used inverted.

By preventing air from flowing out from the vent, the valve also makes it more difficult to refill the bottle by pouring liquid in through the fluid outlet. This is particularly true if the dip tube has been fitted. A transit cap (FIG. 23A (I), white, plain flat top) may be used to seal the fluid outlet and the air vent. This may be removed and re-fitted by the end user. The white draw-off cap (e.g. FIG. 23A (IV), with the hose barbs and rotating collar) may be used to connect flexible tubing to the bottle. In particular, this cap has an unusual/non-typical thread size and cannot be easily fitted to other bottles.

With the design as-shown, the white draw-off cap (with the hose barbs and rotating collar) must be correctly oriented on the red cap to engage the fluid and air paths correctly. To make this connection easier and faster, the fitting action may be modified to a "snap-fit" or "quick release" design. These and other obvious connection means may be routinely engineered by the skilled person, now that the instant disclosure has been made.

With the design as-shown, the user may remove or cut the flexible tubing then attach it to some other draw-off cap and bottle. To prevent this, the flexible tube may have a custom profile that cannot be readily fitted to a standard barbed fitting (without leaking air in). For instance, the tube might have flutes on the inner wall, or other similar "copy-defeating" measures. The connector on the white cap may have a matching shape, and may be permanently connected to the tube.

An alternative tubing profile is the "double D," with two D-shaped tubes formed back-to-back. ϴ This shape prevents the two tubes from being separated. A custom connector that engages with both sides of the tube is required. The bottle draw-off cap(s) would likewise be modified to interface properly with the double D tubes.

Custom tubing of any type requires that the fittings at the applicator be likewise customized. For an anti-counterfeiting measure to function optimally, the applicator must fit the custom tubing, and only the custom tubing. This custom fitting at the applicator can also be combined with a "snap-fit" or "quick release" connector design.

If the dip tube is omitted, for use with the bottle/co-packaging in the inverted position, then it is possible for the user to pour replacement fluid (of another brand) down the fluid passage in the red cap. To prevent this, the dip tube may be fitted at the filling plant. This measure would limit the bottle to upright use only. Upright use may be less likely to result in fluid spills or leaks, and may yield improved routing of the tube to the applicator.

In an embodiment, anti-counterfeiting may be achieved by providing an applicator having two plain holes, aligned with the barrel centerlines, plus a feature to engage a quick-release catch. A plastic adaptor permanently fitted to the double tube may engage with these holes. It will be difficult to fit anything other than the supplied tube and adaptor.

In a rigorous anti-counterfeiting embodiment, the bottles cannot be readily refilled, as the hose profile (flutes or double-D) makes it difficult to fit to a normal barbed fitting. Snap-fit connectors at each end may be fitted to only the disclosed applicator and bottles/co-packaging. There may be restrictions on use, such as upright bottle use only, no rinsing, etc. In an intermediate anti-counterfeiting embodiment, some, but not all elements of the disclosed anti-counterfeiting measures may be present.

Although this invention has been described by way of example and with reference to possible embodiments thereof, it is to be understood that modifications or improvements may be made thereto without departing from the spirit or scope of the invention.

The invention will now be described in the following numbered paragraphs.

1. A multi-chamber, multi-formulation delivery system comprising:
    a. a multi-chamber applicator for delivering multi-formulations to an animal;
    b. a suitable conduit and connectivity for connecting the applicator to fluid packaging; and
    c. a multi-chamber packaging for separately containing and storing formulations.
2. The system of paragraph 1 wherein the applicator comprises:
    a. at least two fluid supply inlets;
    b. at least one outlet;
    c. at least two barrels each having barrel outlets and barrel inlets which are in fluid communication, or selective fluid communication, with the fluid supply inlets;
    d. at least two one way outlet valves, one for each barrel, in fluid communication with the barrel outlets and with the outlets;
    e. at least two pistons, one for each barrel, moveable relative to the barrels and in sealing engagement with the barrels;
    f. a piston actuation means for moving the pistons relative to the barrels;
    g. at least two pressure limiting means for limiting a maximum pressure of fluid entering the barrels from the fluid supply inlets; and optionally
    h. a means for combining the fluids from the at least two barrels into a single outlet.
3. The system of paragraph 2 wherein the applicator (200) is substantially as depicted in FIG. 3 and comprises:
    a. a first barrel (1a) with an outlet (2a);
    b. a one way outlet valve (3a), positioned at or adjacent the barrel outlet (2a), which is in selective fluid communication with an applicator outlet (4) from which fluid is discharged in use;
    c. a second barrel (1b) with an outlet (2b);

d. a one way outlet valve (3*b*), positioned at or adjacent the barrel outlet (2*b*), which is in selective fluid communication with the applicator outlet (4) from which fluid is discharged in use.

4. The system of paragraph 1 or 2 wherein fluid exits each applicator barrel (1) into dispensing conduits (75), and wherein the dispensing conduits (75) intersect at a junction (80) between about 0.5 to about 10.0 inches prior to exiting the outlet (4) as a substantially combined fluid.

5. The system of paragraph 1 or 2 wherein the fluid exits each applicator barrel (1) into dispensing conduits (75), and wherein the conduits do not intersect prior to the fluid being dispensed from the applicator.

6. The system of paragraph 4 wherein the applicator comprises only two valve means (12).

7. The system of paragraph 6 wherein the applicator comprises only two pressure limiting means 10).

8. The system of paragraph 7 wherein fluid flows from the multi-chamber packaging, through supply conduits (76), through the inlet (14), through the pressure limiting means (10), and through the valve means (12), to finally enter the barrel (1).

9. The system of paragraph 7 wherein the pressure limiting means (10) comprises a flexible diaphragm (11) connected to the valve means (12).

10. The system of paragraph 9 wherein a one way valve means (15*a*) is provided to prevent flow from the barrel (1) towards the inlet (14).

11. The system of any one of claim 4 or 6-9, further comprising color-coded conduits that connect the multi-chamber applicator to the multi-chamber packaging, at corresponding color-coded caps.

12. A method for simultaneously administering to an animal in need thereof multiple active ingredient formulations comprising:
    a. connecting a multi-chamber applicator to multi-chamber packaging containing, each of its chambers containing a separate formulation;
    b. loading or priming the multi-chamber applicator with the separate formulations; and
    c. actuating the applicator to dispense the formulations onto or into the animal thereby administering the active ingredients.

13. The method of paragraph 12 wherein at least one of the formulations contain at least one active ingredient which cannot easily be co-formulated with the other active ingredients, which are present in another formulation.

14. The method of paragraph 13 wherein there is no known stable and effective co-formulation of the active ingredients.

15. The method of paragraph 12 wherein the simultaneous administration provides a stronger or synergistic effect, when compared to the effect achieved when the one or more formulations are administered via separate applications.

16. The method of paragraph 12 wherein one incompatible active ingredient is fipronil and the other incompatible active ingredient is amitraz.

17. The method of paragraph 16 wherein the simultaneous administration of fipronil and amitraz has a stronger or synergistic pesticidal effect as compared to a separate administration of fipronil and amitraz.

18. The method of paragraph 17 wherein the stronger effect is extended duration of efficacy against acarids.

19. The method of paragraph 17 wherein the stronger effect is more rapid killing efficacy against acarids.

20. The method of paragraph 17 wherein the stronger effect is reduced development of pesticide resistance.

What is claimed is:

1. A multi-chamber, multi-liquid delivery system comprising:
    an applicator having an outlet for delivering at least two liquids; and
    a dual chamber hose coupled to the applicator for providing parallel fluid communication from packaging, the packaging comprising at least two separate containers that prevents a liquid in each container from mixing with each other prior to entering the applicator, wherein the applicator comprises at least two barrels;
    each barrel comprising:
        an inlet that is coupled to one chamber of the dual chamber hose;
        a one-way valve adjacent to inlet for receiving fluid from the inlet, the one-way valve comprising means for limiting pressure within a respective barrel;
        wherein the pressure limiting means comprises:
            a first valve head and a first valve seat, wherein the first valve head can be moved from a closed position to an open position by movement of a diaphragm; and
            a second valve head and second valve seat, wherein the second valve head is connected to the first valve head and moves with the first valve head, such that a pressure difference across said first valve head is substantially equal to a pressure difference across said second valve head;
        a dispensing conduit that is in fluid communication with the one-way valve;
        a piston for displacing fluid through the dispensing conduit;
    the applicator further comprising:
        a mixing chamber coupled to each dispensing conduit of each barrel for mixing fluid received from each dispensing conduit to create a mixed liquid, the mixing chamber also coupled to the outlet; and
        an actuator coupled to each piston and for moving each piston within a respective barrel when a force is applied to the actuator, each piston when moved dispenses the mixed liquid from the mixing chamber through the outlet, whereby the applicator provides a mechanical advantage in reducing the force needed to actuate the actuator for dispensing the mixed liquid through the outlet.

2. The system of claim 1, further comprising a volume control for adjusting a fluid volume within a respective barrel received from the dual chamber hose.

3. The system of claim 2, wherein the volume control is coupled to the mixing chamber.

4. The system of claim 1, wherein the one-way valve comprises a disc.

5. The system of claim 4, wherein the disc is coupled to a spring.

6. The system of claim 5, wherein the means for limiting pressure comprises a force transfer component coupled to the spring and a ring hub, and a flexible diaphragm that engages the ring hub and a clamp ring.

7. The system of claim 1, wherein the actuator comprises a first handle coupled to a first end of each piston and a second handle coupled to the mixing chamber.

8. The system of claim 1, wherein the two containers are coupled together by a fastening device.

9. The system of claim 8, wherein the fastening device comprises at least one bracket for holding the two containers together when they are coupled to the dual chamber hose.

10. A multi-chamber, multi-formulation delivery system comprising:
an applicator having an outlet for delivering at least two liquid formulations, the applicator comprises at least two barrels;
each barrel comprising:
an inlet;
a one-way valve adjacent to inlet for receiving fluid from the inlet, the one-way valve comprising means for limiting pressure within a respective barrel;
wherein the pressure limiting means comprises:
a first valve head and a first valve seat, wherein the first valve head can be moved from a closed position to an open position by movement of a diaphragm; and
a second valve head and second valve seat, wherein the second valve head is connected to the first valve head and moves with the first valve head, such that a pressure difference across said first valve head is substantially equal to a pressure difference across said second valve head;
a dispensing conduit that is in fluid communication with the one-way valve;
a piston for displacing fluid through the dispensing conduit;
the applicator further comprising:
a mixing chamber coupled to each dispensing conduit of each barrel for mixing fluid received from each dispensing conduit to create a mixed formulation liquid, the mixing chamber also coupled to the outlet; and
an actuator coupled to each piston and for moving each piston within a respective barrel when a force is applied to the actuator, each piston when moved dispenses the mixed formulation liquid from the mixing chamber through the outlet, whereby the applicator provides a mechanical advantage in reducing the force needed to actuate the actuator for dispensing the mixed formulation liquid through the outlet.

11. The system of claim 10, further comprising a dual chamber hose coupled to the applicator for providing parallel fluid communication from packaging.

12. The system of claim 10, wherein the packaging comprises at least two separate containers, each container comprising a different liquid formulation.

13. The system of claim 12, wherein the two containers are coupled together by a fastening device.

14. The system of claim 13, wherein the fastening device comprises at least one bracket for holding the two containers together when they are coupled to the dual chamber hose.

15. The system of claim 10, further comprising a volume control for adjusting a fluid volume within a respective barrel received from the dual chamber hose.

16. The system of claim 14, wherein the volume control is coupled to the mixing chamber.

17. The system of claim 10, wherein the one-way valve comprises a disc.

18. The system of claim 17, wherein the disc is coupled to a spring.

19. The system of claim 18, wherein the means for limiting pressure comprises a force transfer component coupled to the spring and a ring hub, and a flexible diaphragm that engages the ring hub and a clamp ring.

20. The system of claim 10, wherein the actuator comprises a first handle coupled to a first end of each piston and a second handle coupled to the mixing chamber.

21. A multi-chamber, multi-formulation delivery system comprising:
an applicator having an outlet for delivering at least two liquid formulations, the applicator comprises at least two barrels;
each barrel comprising:
an inlet;
a one-way valve adjacent to inlet for receiving fluid from the inlet, the one-way valve comprising a pressure relief device for limiting pressure within a respective barrel;
wherein the pressure limiting device comprises:
a first valve head and a first valve seat, wherein the first valve head can be moved from a closed position to an open position by movement of a diaphragm; and
a second valve head and second valve seat, wherein the second valve head is connected to the first valve head and moves with the first valve head, such that a pressure difference across said first valve head is substantially equal to a pressure difference across said second valve head;
a dispensing conduit that is in fluid communication with the one-way valve;
a piston for displacing fluid through the dispensing conduit;
the applicator further comprising:
a mixing chamber coupled to each dispensing conduit of each barrel for mixing fluid received from each dispensing conduit to create a mixed formulation liquid, the mixing chamber also coupled to the outlet; and
an actuator coupled to each piston and for moving each piston within a respective barrel when a force is applied to the actuator, each piston when moved dispenses the mixed formulation liquid from the mixing chamber through the outlet, whereby the applicator provides a mechanical advantage in reducing the force needed to actuate the actuator for dispensing the mixed formulation liquid through the outlet.

22. The system of claim 21, wherein the one-way valve comprises a disc.

23. The system of claim 22, wherein the disc is coupled to a spring.

24. The system of claim 23, wherein the pressure relief device comprises a force transfer component coupled to the spring and a ring hub, and a flexible diaphragm that engages the ring hub and a clamp ring.

25. The system of claim 21, further comprising a dual chamber hose coupled to the applicator for providing parallel fluid communication from packaging.

26. The system of claim 25, wherein the packaging comprises at least two separate containers, each container comprising a different liquid formulation.

27. The system of claim 26, wherein the two containers are coupled together by a fastening device.

28. The system of claim 27, wherein the fastening device comprises at least one bracket for holding the two containers together when they are coupled to the dual chamber hose.

29. The system of claim 27, wherein the fastening device comprises two brackets for holding the two containers together.

30. The system of claim 24, further comprising a volume control for adjusting a fluid volume within a respective barrel received from the dual chamber hose.

31. The system of claim 30, wherein the volume control is coupled to the mixing chamber.

\* \* \* \* \*